(12) United States Patent
Christensen et al.

(10) Patent No.: US 8,791,236 B2
(45) Date of Patent: *Jul. 29, 2014

(54) METHOD OF ACYLATING A PEPTIDE OR PROTEIN

(71) Applicant: Novo Nordisk A/S, Bagsvaerd (DK)

(72) Inventors: Caspar Christensen, Broenshoej (DK); Rune Severinsen, Roskilde (DK); Anders Klarskov Petersen, Naerum (DK); Steffen Kidal, Koebenhavn (DK); Claus U. Jessen, Slangerup (DK); Peter Madsen, Bagsvaerd (DK); Henrik Valore, Bagsvaerd (DK); Tina Moeller Tagmose, Bellerup (DK); Jan Lindy Soerensen, Havdrup (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/166,148

(22) Filed: Jan. 28, 2014

(65) Prior Publication Data

US 2014/0142280 A1    May 22, 2014

Related U.S. Application Data

(63) Continuation of application No. 13/063,548, filed as application No. PCT/EP2009/061821 on Sep. 11, 2009, now Pat. No. 8,637,647.

(60) Provisional application No. 61/097,645, filed on Sep. 17, 2008.

(30) Foreign Application Priority Data

Sep. 12, 2008  (EP) .................................... 08164261
Jun. 2, 2009  (EP) .................................... 09161650

(51) Int. Cl.
*A61K 38/00* (2006.01)
*C07K 1/107* (2006.01)

(52) U.S. Cl.
CPC .................................. *C07K 1/1077* (2013.01)
USPC .......................................................... 530/333

(58) Field of Classification Search
CPC ........... A61K 47/48023; C07K 14/605; C07K 14/62; C07K 1/1077
See application file for complete search history.

(56) References Cited

U.S. PATENT DOCUMENTS

| | | | |
|---|---|---|---|
| 6,358,924 | B1 | 3/2002 | Hoffmann |
| 6,440,930 | B1 | 8/2002 | Rinella, Jr. |
| 6,583,111 | B1 | 6/2003 | DiMarchi et al. |
| 6,747,006 | B2 | 6/2004 | Efendic |
| 6,844,321 | B2 | 1/2005 | Arentsen |
| 2004/0115759 | A1 | 6/2004 | Dunweber et al. |
| 2007/0207964 | A1 | 9/2007 | Knudsen et al. |
| 2008/0125361 | A1 | 5/2008 | Ludvigsen et al. |
| 2010/0317057 | A1 | 12/2010 | Lau et al. |

FOREIGN PATENT DOCUMENTS

| | | |
|---|---|---|
| EP | 1227107 A1 | 7/2002 |
| WO | 98/08871 | 3/1998 |
| WO | 98/08872 A1 | 3/1998 |
| WO | 99/43708 A1 | 9/1999 |
| WO | 00/55119 A1 | 9/2000 |
| WO | 02/47716 A2 | 6/2002 |
| WO | 03/010186 A2 | 2/2003 |
| WO | 03/028626 A2 | 4/2003 |
| WO | 2004/029077 A2 | 4/2004 |
| WO | 2005/012347 A2 | 2/2005 |
| WO | 2005/054291 A1 | 6/2005 |
| WO | 2006/037810 | 4/2006 |
| WO | 2006/097537 A2 | 9/2006 |
| WO | 2006/097538 | 9/2006 |
| WO | 2007/009894 A2 | 1/2007 |
| WO | 2007/104736 A2 | 9/2007 |
| WO | 2008/087190 A2 | 7/2008 |
| WO | 2009/083549 A1 | 7/2009 |

OTHER PUBLICATIONS

Eldo E Frezza et al., Digestive Diseases and Sciences, "The Multiple Faces of Glucagon-Like Peptide-1-Obesity Appetite, and Stress: What Is Next? A Review", 2007, vol. 52, No. 3, pp. 643-649.

*Primary Examiner* — Thomas Heard
(74) *Attorney, Agent, or Firm* — Richard W. Bork

(57) ABSTRACT

A method for selectively acylating an amino group in a peptide or protein which has two or more reactive nucleophilic functional groups is described.

17 Claims, 1 Drawing Sheet

Purity (260 nm)
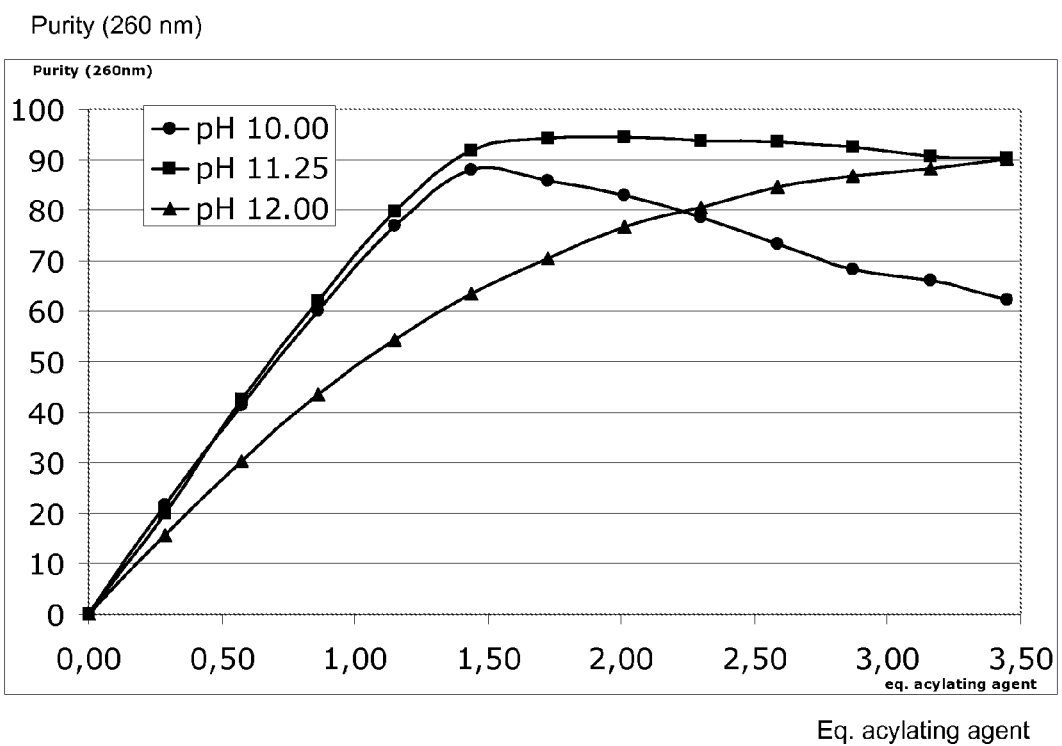
Eq. acylating agent

METHOD OF ACYLATING A PEPTIDE OR PROTEIN

CROSS-REFERENCE TO RELATED APPLICATIONS

This application is a continuation of U.S. application Ser. No. 13/063,548 filed on Apr. 13, 2011, now issued as U.S. Pat. No. 8,637,647 on Jan. 28, 2014, which is a 371 National Phase Filing of International Application No. PCT/EP2009/061821 filed on Sep. 11, 2009 and claims priority under 35 U.S.C. §119 of U.S. Provisional Application No. 61/097,645 filed on Sep. 17, 2008. This application also claims priority of European Patent Application 09161650.8, filed Jun. 2, 2009 and European Patent Application 08164261.3, filed Sep. 12, 2008, all herein incorporated by reference.

FIELD OF THE INVENTION

A method is described for selectively acylating an amino group in a peptide or protein which has two or more reactive nucleophilic functional groups.

BACKGROUND OF THE INVENTION

A large number of peptides have been approved for use in medical practice, and the peptides may be produced in suitable host cells by recombinant DNA technology or they may be produced synthetically by well established peptide synthesis technology. However, native peptides as well as analogues thereof tend to exhibit high clearance rates which are unacceptable for many clinical indications where a high plasma concentration of the peptide is required over a prolonged period of time.

A variety of derivatizations of peptides and peptide analogs have been found to influence the clearance rate of the peptides in a favourable direction as e.g. described in WO98/08871, WO98/08872, WO99/43708, EP 1227107 and WO00/55119. One such derivatization is the introduction of a lipophilic acyl group into the therapeutic peptide causing a desirable protracted profile of action relative to the non-acylated peptide. Hence, less frequent administration of the therapeutic protein improves the patients compliance to the prescribed therapy, and it reduces the amount of peptide to be administered.

In order for therapeutic peptides to be economically viable the cost of producing the peptides as well as the therapeutic dosage of the peptide are pivotal. A major cost during production of therapeutic peptides is the purification steps required to separate the target protein from impurities which are closely related to the target protein. These purification steps are usually performed by chromatography implying expensive chromatography matrices and solvents as well as reduced overall yield.

Introduction of an acyl group into one or more sites of a peptide or protein with more than one nucleophilic atom, such as more than one amine, can give rise to a product mixture of product-related impurities with great resemblance to the desired compound in the crude mixture which gives rise to loss of product and subsequently, a difficult purification step.

It is the aim of the present invention to provide an efficient, robust and economic method for the introduction of lipophilic groups into peptides or proteins via a spacer. Said spacer may e.g. be composed of one or more 8-amino-3,6-dioxaoctanoic acid moietie(s) and glutamic acid. The method is more specific, robust and thus results in higher yields and reduced formation of closely related impurities than other known methods. A significant reduction of the cost of producing the acylated peptides or proteins is achieved. Less expensive acylated peptides are highly desirable for maximizing the number of patients for whom the treatment is available as well as for exploiting the advantages of alternative delivery routes which have lower bioavailability than subcutaneous injection, e.g. transdermal, pulmonal or oral delivery.

The present invention thus provides a method for selectively acylating the epsilonamino group of a lysine residue in a peptide or protein with surprisingly high selectivity.

SUMMARY OF THE INVENTION

A method for selectively acylating one amino group in a peptide or protein which has two or more reactive nucleophilic functional groups is described. In one aspect the method comprises:

a) reacting in an aqueous media a peptide or protein having at least two reactive nucleophilic functional groups with an acylating agent of the general formula I

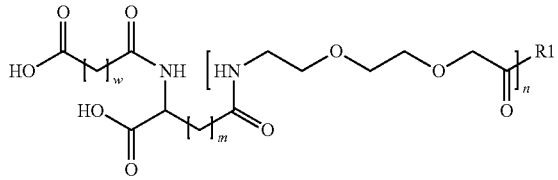

wherein
n is 0-4
m is 1-2
w is 4-20
R1 is a leaving group which when reacting said acylating agent with a free amine facilitates the formation of an amide bond between the carbonyl group attached to R1 and said amine,
wherein pH in the aqueous media is between from pH 8.0 to pH 14; and b) isolating the N-acylated peptide or protein,
wherein an N-acylated peptide or protein is obtained comprising at least one reactive nucleophilic functional group which is not acylated or only partially acylated.

DESCRIPTION OF THE DRAWINGS

FIG. 1: Acylation of [Aib$^8$, Arg$^{34}$]GLP-1(7-37) with 22-carboxy-1-[(2,5-dioxo-1-pyrrolidinyl)oxy]-1,10,19,24-tetraoxo-3,6,12,15-tetraoxa-9,18,23-triazahentetracontan-41-oic acid (compound 1). Illustrated is the purity (as measured by HPLC at 260 nm) dependency of the amount of added acylation agent and the pH. pH values illustrated are: pH 10.00 (-●-), pH 11.25 (-■-), and pH 12.00 (-▲-).

DESCRIPTION OF THE INVENTION

The present method provides a method of securing a selective acylation in a desired position of a peptide or protein. By conducting the acylation reaction of the invention it has surprisingly been shown that a selective acylation can be obtained and thus an impurity profile of the acylation reaction mixture in the form of less undesirable impurities which after termination of the acylation process enables a much easier purification and isolation of the desired selectively acylated product.

Also by the present invention a method of acylation is obtained wherein the acylated peptide or protein is obtained without the use of harsh reagents in or after the acylation step. The obtained product is thus obtained in higher yield and furthermore, due to the convergent method used, by a cheaper method than when using a non-convergent method.

According to the invention an acylation reagent is used which comprises between 1 to 6 OEG spacers, wherein an OEG spacer is a 8-amino-3,6-dioxaoctanoic acid (which may also be named [2-(2-aminoethoxy)ethoxy]acetic acid) moiety of the formula:

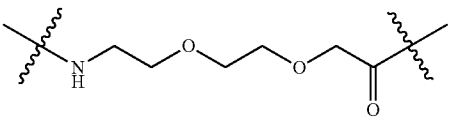 [SMILES: *NCCOCCOCC(*)=O]

When such OEG spacer(s) are present in the acylation agent and a conventional acylation method is used, it is the experience of the inventors that the acylation product is often obtained in low yields. The current invention provides an efficient and robust process of acylation of a peptide or protein with an acylation agent comprising 1 to 6 OEG spacers, wherein a product is provided in high yield.

Acylation is the process of adding an acyl group to a compound. An "acylating agent" is thus herein defined as the compound providing the acyl group to be added to a peptide or protein.

By "selective acylation" or "selectivity" is herein meant that the acylating reagent primarily reacts at one position of the peptide or protein to be acylated compared to other positions in the peptide or protein. For example, the product obtained from acylating a peptide or protein using the acylation method according to the invention results in an acylation product wherein an acylation side chain is attached to only one position of the peptide or protein and not all positions where an acylation could have been obtained had the acylation not been selective. In one aspect of the invention, selectivity is obtained such that acylation of the peptide or protein is obtained such that at least 50% of the acylated peptides or proteins in a reaction mixture are acylated in the preferred acylation site upon completion of the acylation reaction.

In one aspect at least 60% of the acylated peptides or proteins in a reaction mixture are acylated in the preferred acylation site upon completion of the acylation reaction. In another aspect at least 70% of the acylated peptides or proteins are acylated in the preferred acylation site. In another aspect at least 80% of the acylated peptides or proteins are acylated in the preferred acylation site. In another aspect at least 85% of the acylated peptides or proteins are acylated in the preferred acylation site. In another aspect at least 90% of the acylated peptides or proteins are acylated in the preferred acylation site. In another aspect at least 95% of the acylated peptides or proteins are acylated in the preferred acylation site. In another aspect at least 97% of the acylated peptides or proteins are acylated in the preferred acylation site. In another aspect at least 98% of the acylated peptides or proteins are acylated in the preferred acylation site. In another aspect at least 99% of the acylated peptides or proteins are acylated in the preferred acylation site and in yet another aspect approximately all the acylated peptides or proteins in a reaction mixture are acylated in the preferred acylation site upon completion of the acylation reaction.

In one aspect of the invention the preferred acylation site on the peptide or protein is the ε-amino group of a lysine residue such that selective acylation primarily is obtained on the ε-amino group of said lysine.

The term "peptide or protein" as used herein means a compound composed of at least five constituent amino acids connected by peptide bonds. The constituent amino acids may be from the group of the amino acids encoded by the genetic code and they may be natural amino acids which are not encoded by the genetic code, as well as synthetic amino acids. Natural amino acids which are not encoded by the genetic code are e.g., γ-carboxyglutamate, ornithine, phosphoserine, D-alanine and D-glutamine. Synthetic amino acids comprise amino acids manufactured by chemical synthesis, i.e. D-isomers of the amino acids that are encoded by the genetic code such as D-alanine and D-leucine, Aib (aaminoisobutyric acid), Abu (α-aminobutyric acid), Tle (tert-butylglycine), β-alanine, 3-aminomethyl benzoic acid, anthranilic acid.

The 22 proteogenic amino acids are:
Alanine, Arginine, Asparagine, Aspartic acid, Cysteine, Cystine, Glutamine, Glutamic acid, Glycine, Histidine, Hydroxyproline, Isoleucine, Leucine, Lysine, Methionine, Phenylalanine, Proline, Serine, Threonine, Tryptophan, Tyrosine, Valine.

Thus a non-proteogenic amino acid is a moiety which can be incorporated into a peptide or protein via peptide bonds but is not a proteogenic amino acid. Examples are γcarboxyglutamate, ornithine, phosphoserine, the D-amino acids such as D-alanine and D-glutamine, Synthetic non-proteogenic amino acids comprise amino acids manufactured by chemical synthesis, i.e. D-isomers of the amino acids encoded by the genetic code such as D-alanine and D-leucine, Aib (α-aminoisobutyric acid), Abu (α-aminobutyric acid), ornithine, Dap (2,3-diaminopropionic acid), Dab (2,4-diaminobutanoic acid), Tle (tert-butylglycine), 3-aminomethyl benzoic acid, anthranilic acid, des-amino-Histidine, the beta analogs of amino acids such as β-alanine etc. D-histidine, desamino-histidine, 2-amino-histidine, β-hydroxyhistidine, homohistidine, $N^\alpha$-acetyl-histidine, α-fluoromethyl-histidine, α-methyl-histidine, β-pyridylalanine, 2-pyridylalanine or 4-pyridylalanine, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

The term "analogue" as used herein referring to a peptide or protein means a modified peptide or protein wherein one or more amino acid residues of the peptide or protein have been substituted by other amino acid residues and/or wherein one or more amino acid residues have been deleted from the peptide or protein and/or wherein one or more amino acid residues have been deleted from the peptide or protein and or wherein one or more amino acid residues have been added to the peptide or protein. Such addition or deletion of amino acid residues can take place at the N-terminal of the peptide or protein and/or at the C-terminal of the peptide or protein. A simple system is often used to describe analogues: For example [$Aib^8$, $Arg^{34}$]GLP-1(7-37) designates a GLP-1(7-37) analogue wherein the naturally occurring alanine at position 8 is substituted with alpha-aminoisobutyric acid and lysine at position 34 has been substituted with arginine. All amino acids for which the optical isomer is not stated is to be understood to mean the L-isomer. In aspects of the invention a maximum of 17 amino acids have been modified. In aspects of the invention a maximum of 15 amino acids have been modified. In aspects of the invention a maximum of 10 amino acids have been modified. In aspects of the invention a maximum of 8 amino acids have been modified. In aspects of the invention a maximum of 7 amino acids have been modified. In aspects of the invention a maximum of 6 amino acids have been modified. In aspects of the invention a maximum of 5 amino acids have been modified. In aspects of the invention a maximum of 4 amino acids have been modified. In aspects of the invention a maximum of 3 amino acids have been modified. In aspects of the invention a maximum of 2 amino acids have been modified. In aspects of the invention 1 amino acid has been modified.

In one aspect of the invention, the C-terminal of the derivative according to the invention may be terminated as either an acid or amide. In one aspect, the C-terminal of the derivative of the invention is an amide. In another aspect, the C-terminal of the derivative of the invention is an acid.

It should be understood that the peptide or protein should carry at least two reactive nucleophilic functional groups, for example amino groups being e.g. the N-terminal amino group and/or a side chain amino group. The peptides or proteins may comprise amino acids which are not encoded by the genetic code, such as D-amino acids, 3-hydroxyproline, Aib (α-aminoisobutyric acid), ornithine, Dap (2,3-diaminopropionic acid), Dab (2,4-diaminobutanoic acid) and pentylglycine. Particularly interesting are amino groups of lysine, ornithine, Dap and Dab amino acid residues. The method is particular relevant for the N-acylation of the ε-amino group of lysine residues.

Herein, the naming of the peptides or proteins is done according to the following principles: The names are given as mutations and modifications (acylations) relative to the parent peptide or protein such as human GLP-1 or human insulin. For the naming of the acyl moiety, the naming is done according to IUPAC nomenclature and in other cases as peptide nomenclature. For example, naming the acyl moiety:

with the acylating reagent), serine (where the hydroxyl group can react with the acylating reagent), threonine (where the hydroxyl group can react with the acylation reagent), thiol groups from e.g. cysteine (where the thiol group can react with the acylating reagent) amino-groups such as but not limited to e.g. the Nα-terminus amine of the peptide or protein, lysine (where the ε-amino group can react with the acylating reagent), and other nucleophiles within the peptide or protein such as but not limited to arginine (where the guanidine group can react with the acylating reagent) and histidine (where the imidazole group can react with the acylating reagent).

In one aspect a peptide or protein to be acylated according to the invention has at least two free amino groups. In another aspect the peptide or protein has between 2 and 10 free amino groups, for example between 2 and 8 free amino groups, between 2 and 6 free amino groups, between 2 and 4 free amino groups or between 2 and 3 free amino groups. In one aspect the peptide or protein has 2 free amino groups.

When used herein the term "free amino group" shall mean a primary or secondary amino group which under the given reaction conditions reacts with the acylating agent to form a covalent bond.

The term "partially acylated" when used in connection with at least one free amino group of an N-acylated peptide, shall mean that in a reaction mixture comprising said N-acylated peptide, a part of the peptides in the reaction mixture have at least one free amino group which is not connected to an acylation moiety and another part of the peptides have the same at least one amino group which is connected to an acylation moiety.

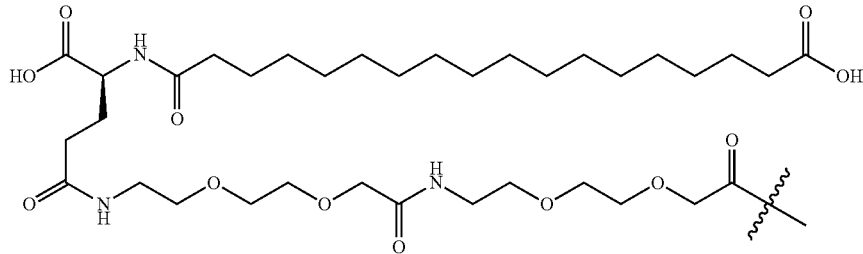 [SMILES: *C(=O)COCCOCCNC(=O)COCCOCCNC(=O)CC[C@H](NC(=O)CCCCCCCCCCCCCCCCC(=O)O)C(=O)O]

can be e.g. "octadecanedioyl-γGlu-OEG-OEG", or "17-carboxyheptadecanoyl-γGlu-OEGOEG", wherein
OEG is short hand notation for the amino acid —NH(CH$_2$)$_2$O(CH$_2$)$_2$OCH$_2$CO—, and γGlu (or gGlu) is short hand notation for the amino acid gamma glutamic acid moiety.

In one aspect a peptide or protein to be acylated according to the invention has at least two reactive nucleophilic functional groups which can react with the acylating reagent. In another aspect the peptide or protein has between 2 and 10 reactive nucleophilic functional groups, for example between 2 and 8 reactive nucleophilic functional groups, between 2 and 6 reactive nucleophilic functional groups, between 2 and 4 reactive nucleophilic functional groups or between 2 and 3 reactive nucleophilic functional groups. In one aspect the peptide or protein has 2 reactive nucleophilic functional groups.

Reactive nucleophilic functional groups are herein to be understood as chemical functionalities that under the given reaction conditions react with the acylating reagent to form a stabile covalent bond. Examples of such reactive nucleophilic functional groups include, but are not limited to, hydroxyl-groups from e.g. tyrosine (where the hydroxyl group can react The peptide or protein to be acylated may comprise one or more lysine (Lys) amino acid residues. In one aspect selection of the acylation position(s) is between ε-amino group(s) of lysine group(s) in the peptide or protein and the α-amino-group(s) in the Nterminal(s) of the peptide or protein, where acylation primarily is obtained on the one or more ε-amino group(s) rather than on the α-amino-group(s) in the N-terminal(s) of the peptide or protein. In one aspect the peptide or protein comprises one lysine (Lys) amino acid residue and one or more N-terminal α-amino-groups, where acylation is selective on the ε-amino group of the Lys amino acid. In one further aspect the peptide or protein comprises one lysine (Lys) amino acid residue and one N-terminal α-amino-group, where acylation is selective on the ε-amino group of the Lys amino acid.

The "reaction mixture" is herein to be understood as the mixture of solvents and reagents used when reacting the acylating agent with the peptide or protein. The reaction mixture should be aqueous, i.e. water being present in the reaction mixture.

To obtain selectivity of the acylation, the pH of the aqueous reaction mixture is adjusted to between pH 8 and pH 14. In one aspect pH of the reaction medium is between pH 9 and pH 13. In another aspect the pH is between pH 10 and pH 12. In another aspect the pH is between pH 12 and pH 13. In another aspect the pH is between pH 10 and pH 13. In another aspect the pH is between pH 10.5 and pH 12.0 or between pH 11.0 and pH 11.5, and in yet another aspect pH is about pH 11.0-11.3. In still another aspect pH is between pH 11 and pH 12, such as between pH 11.5 and pH 12 or between pH 11.5 and pH 11.8 or between pH 11.5 and pH 12.5. In one aspect pH is about pH 11.5.

The terms "about" or "approximately" as used herein means in reasonable vicinity of the stated numerical value, such as plus or minus 10%, or for pH values plus or minus 0.2.

By adjusting the pH according to the invention, a surprisingly robust acylation reaction is obtained. By "robust" or "robustness" when referring to the acylation reaction is herein meant that the yield and selectivity obtained when using the acylation process according to the invention are high and not sensitive to the amount of acylating agent added, when the acylating agent is added in excess (see e.g. FIG. 1).

The pH of the reaction mixture may be controlled by means known to the person skilled in the art. For example a simple pH-meter may be used to measure the pH and acid or base may be added manually to adjust the pH, or a pH-meter with a feed-back mechanism, which can control the pH of the solution, may be used.

Acids suitable for adjusting the pH include but are not limited to: Hydrochloric acid, sulphuric acid and acetic acid.

Bases suitable for adjusting the pH include, but are not limited to: Tertiary amine bases such as, but not limited to, triethylamine or diisopropylethylamine, N-methylmorpholine, alkalimetal hydroxides such as, but not limited to, lithium hydroxide, sodium hydroxide, potassium hydroxide or cesium hydroxide and alkali carbonates such as, but not limited to, potassium carbonate, sodium carbonate, lithium carbonate, potassium hydrogen carbonate, sodium hydrogen carbonate or lithium hydrogen carbonate.

In one aspect of the invention the reaction mixture comprises a buffer. In one aspect of the invention the buffer is selected from the group consisting of: Phosphate buffer, Sodium carbonate buffer, Bicine N,N-Bis(2-hydroxyethyl) glycine buffer, HEPPS buffer (3-[4-(2-Hydroxyethyl)-1-piperazinyl]propanesulfonic acid buffer), HEPES buffer (4-(2-Hydroxyethyl)-1-piperazineethanesulfonic acid buffer), MOPS buffer (3-(N-Morpholino)propanesulfonic acid buffer) and TEA buffer (Triethylamine buffer).

The acylation reagent should preferably be either added to the solution as a solid or be dissolved in an appropriate inert solvent and then added as a solution. Examples of inert solvents are e.g. but not limited to N-methylpyrrolidinone, dimethylformamide, dimethylacetamide, acetonitril, tetrahydrofuran, and dimethyl sulfoxide. The acylation agent may be added in an amount of e.g. 0.5-20 equivalents such as 1-20 equivalents, 1-5 equivalents or 1-3 equivalents relative to the number of reactive nucleophilic functional groups such as amino groups to be acylated. For example if adding 1 mole peptide or protein having 1 amino group to be acylated, the acylating agent can be added in an amount from 0.5 moles to 20 moles such as from 1 to 5 moles. It has surprisingly been found that when using the method according to the invention, selectivity and robustness may be achieved even when adding a large excess of acylation reagent. In one aspect the acylation agent is added in an amount of 1-4 equivalents, alternatively 1.2-3.0 equivalents, alternatively 1.4-2.0 equivalents. In one aspect the acylation agent is added in an amount of about 1.75 equivalents. When dissolved in an inert solvent, the acylation agent may be added in the concentration of at least 10 mg acylation reagent per ml inert solvent. In one aspect the concentration of the acylation reagent in the inert solvent is between 10 mg/ml and 1000 mg/ml inert solvent. In another aspect the concentration is between 50 mg/ml and 250 mg/ml inert solvent. In yet another aspect the concentration of the acylation reagent in the inert solvent is about 100 mg/ml inert solvent.

The temperature of the reaction mixture during the acylation procedure may be between −5° C. and 50° C. such as between 0° C. and 50° C. In one aspect the temperature is between 5° C. and 40° C. In another aspect the temperature is between 10° C. and 30° C. In yet another aspect the temperature is about 20° C. In still another aspect the temperature is between −5° C. and 10° C. In still another aspect the temperature is between 0° C. and 5° C. In still another aspect the temperature is between 2 and 5° C. In one aspect of the invention the reaction mixture is kept at room temperature.

The acylation reagent may be added with stirring or agitation to the reaction mixture over a period of between 0 min and 480 min such as over a period of between 10 and 240 min. In one aspect the reagent is added over a period of between 10 and 180 min. In another aspect the reagent is added over a period of between 20 and 120 min. In yet another aspect the reagent is added over a period of about 30 min. In yet another aspect the reagent is added over a period of about 60 min. In still another aspect the reagent is added over a period of between 30 and 60 minutes.

After addition of the acylation reagent, the acylation mixture may be left (optionally with stirring or agitation) for reaction for between 0 min and 1440 min (i.e. 24 hours) such as between 0 and 720 min before the reaction is stopped by regulating the pH to about 7.5-8.0 or lower. In one aspect the acylation mixture is left for between 15 and 240 min. In another aspect the acylation mixture is left for between 30 and 120 min. In another aspect the acylation mixture is left for between 0 and 15 min. In yet another aspect the acylation mixture is left for about 0 min, i.e. the reaction is stopped immediately after addition of the acylation reagent. In yet another aspect the acylation mixture is left for about 30 min. In yet another aspect the acylation mixture is left for about 60 min. In still another aspect the acylation mixture is left for between 30 and 60 minutes.

The peptide or protein should preferably be present in the reaction mixture in a concentration of at least 5.0 mg/ml. In one aspect the concentration of the protein or peptide is between 5.0 mg/ml and 250 mg/ml reaction mixture. In yet another aspect the concentration of the protein or peptide is between 10 mg/ml and 100 mg/ml. In yet another aspect the concentration of the protein or peptide is between 10 mg/ml and 75 mg/ml. In yet another aspect the concentration of the protein or peptide is between 10 mg/ml and 50 mg/ml. In yet another aspect the concentration of the protein or peptide is between 10 mg/ml and 30 mg/ml. In yet another aspect the concentration of the protein or peptide is between 15 mg/ml and 25 mg/ml. In yet another aspect the concentration of the protein or peptide is between 10.0 mg/ml and 20.0 mg/ml. In still another aspect the concentration of the protein or peptide is approximately 12.5 mg/ml. In still another aspect the concentration of the protein or peptide is approximately 20 mg/ml.

The reaction mixture may comprise further components and/or solvents. For example inert solvents such as polar aprotic solvents including, but not limited to, N-methylpyrrolidinone, dimetylformamide, dimethylacetamide, acetonitril, tetrahydrofuran and dimethyl sulfoxide may be present in the reaction mixture. In one aspect an inert solvent is present in an amount from 0-25% v/v of the total amount of the reaction mixture. In another aspect an inert solvent is present in an amount from 0-10% v/v or 0-5% v/v. In another aspect an inert solvent is present in an amount from 4-20% v/v or 4-10% v/v. In yet another aspect an inert solvent is present in an amount from 4-5% v/v. In one aspect an inert solvent is present and is N-methylpyrrolidinone.

In one aspect the reaction mixture further comprises compounds and/or salts which were present in the peptide or protein to be acylated or in the acylation reagent before the peptide or protein and acylation reagent were dissolved in the reaction media. For example salts or other compounds that are present in the peptide or protein e.g. via ionic bonds as a result of the peptide or protein synthesis may be present in the reaction mixture in the method according to the invention. Examples of such compounds and/or salts include but is not limited to: Trifluoroacetic acid (TFA), acetic acid, hydrochloric acid (HCl), citric acid, phosphorus acid, sulfonic acid, sodium salt, potassium salt and lithium salt.

In one aspect of the invention, the acyl group to be introduced into the peptide or protein such as the ε-amine group of a Lys residue of the peptide or protein comprises an albumin binding residue, i.e. a residue which under in vivo conditions binds to albumin when attached to a peptide or protein.

In one aspect, the albumin binding residue is a lipophilic residue. In a further aspect, the lipophilic residue is attached to the peptide or protein via a linker.

In a further aspect of the invention, the albumin binding residue is negatively charged at physiological pH. In another aspect of the invention, the albumin binding residue comprises a group which can be negatively charged. One preferred group which can be negatively charged is a carboxylic acid group.

In one aspect, the albumin binding residue is an α,ω-fatty diacid residue

In a further aspect of the invention, the α,ω-fatty diacid residue of the lipophilic residue has from 6 to 40 carbon atoms, from 8 to 26 carbon atoms or from 8 to 22 carbon atoms.

In another aspect of the invention, the albumin binding residue is an acyl group of a straight-chain or branched alkane α,ω-dicarboxylic acid. In a further aspect the albumin binding residue is an acyl group of a straight-chain or branched alkane α,ω-dicarboxylic acid which includes an amino acid portion such as e.g. a gamma-Glu portion. In yet a further aspect the albumin binding residue is an acyl group of a straight-chain or branched alkane α,ω-dicarboxylic acid which includes two amino acid portions such as e.g. a gamma-Glu portion and a 8-amino-3,6-dioxaoctanoic acid (OEG) portion. In yet a further aspect the albumin binding residue is an acyl group of a straight-chain or branched alkane α,ω-dicarboxylic acid which includes more amino acid portions such as e.g. one gamma-Glu portion and consecutive 8-amino-3,6-dioxaoctanoic acid (OEG) portions.

In the method according to the invention, a peptide or protein which has at least two reactive nucleophilic functional groups is reacted with an acylating agent of the general formula I

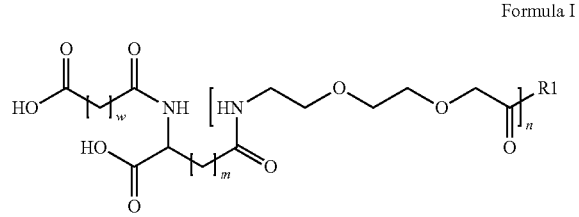

Formula I wherein
n is 0-4, alternatively 2
m is 1-2, alternatively 2
w is 4-20, alternatively 10-20, alternatively 14-18, alternatively 16
R1 is a leaving group which when reacting said acylating agent with a free amine facilitates the formation of an amide bond between the carbonyl group attached to R1 and said amine The acylating agent may be in the form of a pure enantiomer wherein the stereo configuration of the chiral amino acid moiety is either D or L (or if using the R/S terminology: either R or S) or it may be in the form of a mixture of enantiomers (D and L/R and S). In one aspect of the invention the acylating agent is in the form of a mixture of enantiomers. In one aspect the acylating agent is in the form of a pure enantiomer. In one aspect the chiral amino acid moiety of the acylating agent is in the D form. In one aspect the chiral amino acid moiety of the acylating agent is in the L form.

R1 in formula I may be any group which when reacting the acylating agent with a free amine acts as a leaving group, such that an amide bond between the carbonyl group attached to R1 and the amine is formed. For example R1 together with the carbonyl to which R1 is attached may designate an anhydride, a carboxylic acid halide or an ester.

In one aspect R1 in formula I together with the carbonyl to which R1 is attached designate an ester such as an activated ester or an activated N-hydroxy imide ester. Each of these esters constitutes alternative aspects of the present invention.

Activated esters and activated N-hydroxy imide esters are well known in the art of organic chemistry (especially in peptide chemistry) as functional groups which are used in acylation of amino, thio and hydroxy groups. Within the context of the present invention, the term "activated ester or an activated N-hydroxy imide ester" is intended to mean an ester functionalised form of a carboxylic acid group suitable for acylating an amine, preferably a primary amine. It should thus be understood, that selectivity for acylation of primary amines is preferred over acylating of hydroxy and thio groups. Activated N-hydroxy imide esters are especially preferred.

The term "activated" acylating agent means an acylating agent which has been activated using general techniques as e.g. described in "Amide bond formation and peptide coupling" (Tetrahedron 61(46), 10827-10852, 2005).

Examples of activated acylating agents include, but are not limited to acid chlorides, acid bromides, acid fluorides, symmetrical anhydrides, mixed anhydrides, carboxylic acids activated using common carbodiimides such as, but not limited to, diisopropylcarbodiimide (DIPCDI), N,N=dicyclohexylcarbodiimide (DCC), 1-ethyl-3-(3'-dimethylaminopropyl)carbodiimide hydrochloride (EDC). Furthermore included, but not limited to, are carboxylic acids using the aforementioned carbodiimides and an additive such as, but not limited to, N-hydroxysuccinimide (HOSu), N-hydroxybenzotriazol (HOBt), 1-Hydroxy-7-azabenzotriazol, 6-chloro-N-hydroxybenzotriazol (HOAt), 3-Hydroxy-3,4-dihydro-4-oxo-1,2,3-benzotriazine (DhbtOH) or p-nitrophenol (PNP). Also included, but not limited to, are carboxylic acids activated with an uronium salt or a phosphonium salt, such as but not limited to, O-Benzotriazole-N,N,N',N'-tetramethyluronium hexafluorophosphate (HBTU), O(Benzotriazol-1-yl)-N,N,N',N'-tetramethyluronium tetrafluoroborate (TBTU), 2-(6-Chloro-1H benzotriazole-1-yl)-1,1,3,3-tetramethylaminium hexafluorophosphate (HCTU), 2-(6-Chloro-1H-benzotriazole-1-yl)-1,1,3,3-tetramethylaminium tetrafluoroborate (TCTU), 2-(1H-7-Azabenzotriazol-1-yl)-1,1,3,3-tetramethyl uronium hexafluorophosphate (HATU), 2-(3,4-Dihydro-4-oxo-1,2,3-benzotriazin-3-yl)-N,N,N',N'-tetramethyluronium hexafluorophosphate (HDBTU), 2-Succinimido-1,1,3,3-tetramethyluronium hexafluorophosphate (HSTU), N,N,N',N'-Tetramethyl-O-(succinimidyl)uronium tetrafluoroborate (TSTU), 2-(endo-5-norbornene-2,3-dicarboxymido)-1,1,3,3-tetramethyluronium hexafluorophosphate (HNTU),1-benzotriazolyoxytris-(dimethylamino) phosphonium hexafluorophosphate (BOP) or benzotriazol-1-yl-oxytripyrrolidinophosphonium hexafluorophosphate (PYBOP). Other activated esters include, but are not limited to, esters of N-hydroxysuccinimide (NHS ester), p-nitrophenol (PNP ester), N-Hydroxy-5-norbornene-2,3-dicarboxylimide (HONB-ester), Npentafluorophenol ester (PfP-ester), 2,4-dinitrophenyl ester, 4-nitrophenyl ester, 3-hydroxy-3,4-dihydro-4-oxo-1,2,3-benzotriazine (HODhbt), carbonyldiimidazole (CDI) or N-ethyl-5-phenylisoxazolium-3'-sulfonate (NEPIS), preferably a N-hydroxysuccinimide ester, p-nitrophenol or a HOBt ester or a derivative thereof using reaction conditions as e.g. described in the references: Organic Synthesis on solid Phase (Florencio Zaragoza Dörwald, Wiley-VCH Verlag GmbH, D-69469 Weinheim, 2000), Novabiochem Catalog (Merck Biosciences 2006/2007) and Fmoc Solid Phase Peptide Synthesis (Edited by W. C. Chan and P. D. White, Oxford University Press, 2000, ISBN 0-19-963724-5).

The acylating agent of the formula I is used in a slight deficiency, equal amount or slight excess relative to the number of amino groups of the peptide or protein to be acylated. The ratio may e.g. be from 1:0.5 relative to the number of reactive nucleophilic functional groups such as amino groups to be acylated according to the procedure and is typically from 1:1 to 1:20 with equal amount or an excess of the acylating agent, alternatively from 1:1.1 to 1:5 relative to the number of reactive nucleophilic functional groups such as amino groups to be acylated according to the procedure. The acylating agent may be added to the reaction mixture as a solid or it may be added to the reaction mixture as a solution. When the acylating agent is added as a solution it is dissolved in inert solvent, wherein the term "inert" means inert to the acylating agent. The stability of the acylating agent may be improved (i.e. stabilized) by adding an acid.

In one aspect of the method, the acylating agent is added to the reaction mixture as a solid.

In one aspect of the method, said peptide or protein used as starting material for step a) has a peptide or protein purity of at least 80%, at least 90%, at least 93%, at least 95%, or at least 97% as determined by HPLC.

As a typical example, the reaction in step (a) is performed using the peptide or protein and the acylating agent of the formula I in a 1:1 to 1:5 molar ratio. The peptide or protein is typically pre-dissolved in water at −10-30° C. such as 0-30° C. and the pH is adjusted to the desired pH level using an alkalimetal hydroxide (e.g. sodium hydroxide or potassium hydroxide) or a tertiary amine base (e.g. triethyl amine or N,N-diisopropylethylamine). The pH value may be further adjusted using acids (e.g. hydrochloric acid, sulfonic acid or acetic acid), but the temperature is preferably within the above range. Alternatively the peptide or protein is pre-dissolved directly in to an aqueous solution comprising an appropriate amount of the relevant acid or base. The acylating agent is subsequently added as a solid or as a solution. The reaction is typically allowed to proceed to completion (can be monitored by HPLC) which is typically obtained from instantly and up to within 24 hours, such as 0.2-6 hours, before addition of an acid, e.g. hydrochloric acid, sulfonic acid or acetic acid, to pH 6.5-9.0 such as to e.g. pH 7.5-8.0. The product is typically isolated and purified by ion-exchange chromatograhpy, HPLC, and/or is precipitated by isoelectric pH.

The present invention is especially suitable for the acylation of peptides or proteins suitable for treating e.g. diabetes such as glucagon-like peptides and insulins.

In one aspect the peptide or protein to be acylated is a glucagon-like peptide.

The term "glucagon-like peptide" as used herein means the glucagon family of peptides, exendins and analogues thereof. The glucagon family of peptides are encoded by the preproglucagon gene and encompasses three small peptides with a high degree of homology, i.e. glucagon (1-29), GLP-1 (1-37) and GLP-2 (1-33). Exendins are peptides expressed in lizards and like GLP-1, are insulinotropic. Examples of exendins are exendin-3 and exendin-4.

The terms GLP-1, GLP-2, exendin-3 and exendin-4 are known to a person skilled in the art. For example "GLP-1 compound" or "GLP-1 peptide" as used herein means human GLP-1(7-37), insulinotropic analogue thereof and insulinotropic derivatives thereof. Non-limiting examples of GLP-1 analogues are GLP-1(7-36) amide, $Arg^{34}$-GLP-1(7-37), $Aib^8Arg^{34}$-GLP-1(7-37), $Gly^8$-GLP-1(7-37), $Val^8$-GLP-1(7-36)-amide and $Val^8Asp^{22}$-GLP-1(7-37). Non-limiting examples of GLP-1 derivatives are desamino-$His^7$, $Arg^{26}$, $Lys^{34}(N^\epsilon$-($\gamma$-Glu($N^\alpha$-hexadecanoyl)))-GLP-1(7-37), desamino-$His^7$, $Arg^{26}$, $Lys^{34}(N^\epsilon$-octanoyl)-GLP-1(7-37), $Arg^{26,34}$, $Lys^{38}(N^\epsilon$-($\omega$-carboxypentadecanoyl))-GLP-1(7-38), $Arg^{26,34}$, $Lys^{36}(N^\epsilon$-($\gamma$-Glu($N^\alpha$-hexadecanoyl)))-GLP-1(7-36) and $Arg^{34}$, $Lys^{26}(N^\epsilon$-($\gamma$-Glu($N^\alpha$-hexadecanoyl)))-GLP-1(7-37).

In one aspect the glucagon-like peptide according to the invention is dipeptidyl aminopeptidase IV protected. In another aspect the GLP-1 analogue according to the invention is dipeptidyl aminopeptidase IV protected.

The term "dipeptidyl aminopeptidase IV protected" as used herein means a glucagon-like peptide, e.g. a GLP-1 analogue, which is more resistant to dipeptidyl aminopeptidase IV (DPP-IV) than the native compound, e.g. GLP-1(7-37). Such protection may be obtained by e.g. mutations and/or derivatization of the native compound. Resistance of a GLP-1 compound towards degradation by dipeptidyl aminopeptidase IV is determined by the following degradation assay:

Aliquots of the GLP-1 compound (5 nmol) are incubated at 37° C. with 1 µL of purified dipeptidyl aminopeptidase IV corresponding to an enzymatic activity of 5 mU for 10-180 minutes in 100 µL of 0.1 M triethylamine-HCl buffer, pH 7.4. Enzymatic reactions are terminated by the addition of 5 µL of 10% trifluoroacetic acid, and the peptide degradation products are separated and quantified using HPLC analysis. One method for performing this analysis is: The mixtures are applied onto a Vydac C18 widepore (30 nm pores, 5 µm particles) 250×4.6 mm column and eluted at a flow rate of 1 ml/min with linear stepwise gradients of acetonitrile in 0.1% trifluoroacetic acid (0% acetonitrile for 3 min, 0-24% acetonitrile for 17 min, 24-48% acetonitrile for 1 min) according to Siegel et al., Regul. Pept. 1999; 79:93-102 and Mentlein et al. Eur. J. Biochem. 1993; 214:829-35. Peptides and their degradation products may be monitored by their absorbance at 220 nm (peptide bonds) or 280 nm (aromatic amino acids), and are quantified by integration of their peak areas related to those of standards. The rate of hydrolysis of a GLP-1 compound by dipeptidyl aminopeptidase IV is estimated at incubation times which result in less than 10% of the GLP-1 compound being hydrolysed.

The term "insulinotropic" as used herein referring to a glucagon-like peptide means the ability to stimulate secretion of insulin in response to an increased plasma glucose level. Insulinotropic glucagon-like peptides are agonists of the GLP-1 receptor. The insulinotropic property of a compound may be determined by in vitro or in vivo assays known in the art. The following in vitro assay may be used to determine the insulinotropic nature of a compound such as a glucagon-like peptide. Preferably insulinotropic compounds exhibit an $EC_{50}$ value in the below assay of less than 5 nM, even more preferably an $EC_{50}$ value of less than 500 pM.

Baby hamster kidney (BHK) cells expressing the cloned human GLP-1 receptor (BHK 467-12A) are grown in DMEM media with the addition of 100 IU/mL penicillin, 100 μL/mL streptomycin, 10% foetal calf serum and 1 mg/mL Geneticin G-418 (Life Technologies). Plasma membranes are prepared by homogenization in buffer (10 mM Tris-HCl, 30 mM NaCl and 1 mM dithiothreitol, pH 7.4, containing, in addition, 5 mg/mL leupeptin (Sigma), 5 mg/L pepstatin (Sigma), 100 mg/L bacitracin (Sigma), and 16 mg/L aprotinin (CalbiochemNovabiochem, La Jolla, Calif.)). The homogenate is centrifuged on top of a layer of 41% W/v sucrose. The white band between the two layers is diluted in buffer and centrifuged. Plasma membranes are stored at −79° C. until used.

The functional receptor assay is carried out by measuring cAMP as a response to stimulation by the insulinotropic peptide or insulinotropic compound. Incubations are carried out in 96-well microtiter plates in a total volume of 140 mL and with the following final concentrations: 50 mM Tris-HCl, 1 mM EGTA, 1.5 mM $MgSO_4$, 1.7 mM ATP, 20 mM GTP, 2 mM 3-isobutyl-1-methylxanthine (IBMX), 0.01% w/v Tween-20, pH 7.4. Compounds are dissolved and diluted in buffer. GTP is freshly prepared for each experiment: 2.5 μg of membrane is added to each well and the mixture is incubated for 90 min at room temperature in the dark with shaking. The reaction is stopped by the addition of 25 mL 0.5 M HCl. Formed cAMP is measured by a scintillation proximity assay (RPA 542, Amersham, UK). A dose-response curve is plotted for the compound and the $EC_{50}$ value is calculated using GraphPad Prism software.

The term "prodrug of an insulinotropic compound" as used herein means a chemically modified compound which following administration to the patient is converted to an insulinotropic compound. Such prodrugs are typically amino acid extended versions or esters of an insulinotropic compound.

The term "exendin-4 compound" as used herein is defined as exendin-4(1-39), insulinotropic fragments thereof, insulinotropic analogs thereof and insulinotropic derivatives thereof. Insulinotropic fragments of exendin-4 are insulinotropic peptides for which the entire sequence can be found in the sequence of exendin-4 and where at least one terminal amino acid has been deleted. Examples of insulinotropic fragments of exendin-4(1-39) are exendin-4(1-38) and exendin-4(1-31). The insulinotropic property of a compound may be determined by in vivo or in vitro assays well known in the art. For instance, the compound may be administered to an animal and monitoring the insulin concentration over time. Insulinotropic analogs of exendin-4(1-39) refer to the respective molecules wherein one or more of the amino acids residues have been exchanged with other amino acid residues and/or from which one or more amino acid residues have been deleted and/or from which one or more amino acid residues have been added with the proviso that said analogue either is insulinotropic or is a prodrug of an insulinotropic compound. An example of an insulinotropic analog of exendin-4(1-39) is $Ser^2Asp^3$-exendin-4(1-39) wherein the amino acid residues in position 2 and 3 have been replaced with serine and aspartic acid, respectively (this particular analog also being known in the art as exendin-3). Insulinotropic derivatives of exendin-4 (1-39) and analogs thereof are what the person skilled in the art considers to be derivatives of these peptides, i.e. having at least one substituent which is not present in the parent peptide molecule with the proviso that said derivative either is insulinotropic or is a prodrug of an insulinotropic compound. Examples of substituents are amides, carbohydrates, alkyl groups, esters and lipophilic substituents. An example of an insulinotropic derivative of exendin-4(1-39) and analog thereof is $Tyr^{31}$-exendin-4(1-31)-amide.

The term "stable exendin-4 compound" as used herein means a chemically modified exendin-4(1-39), i.e. an analogue or a derivative which exhibits an in vivo plasma elimination half-life of at least 10 hours in man, as determined by conventional methods.

The term "dipeptidyl aminopeptidase IV protected exendin-4 compound" as used herein means an exendin-4 compound which is more resistant towards the plasma peptidase dipeptidyl aminopeptidase IV (DPP-IV) than exendin-4, as determined by the assay described under the definition of dipeptidyl aminopeptidase IV protected GLP-1 compound.

The GLP-1 analogues may be such wherein the naturally occurring Lys at position 34 of GLP-1(7-37) has been substituted with Arg.

Also, derivatives of precursors or intermediates of insulinotropic peptides are covered by the invention.

In one aspect of the invention the glucagon-like peptide is insulintropic. In a further aspect the insulintropic glucagon-like peptide is selected from the group consisting of GLP-1, GLP-2, exendin-4, exendin-3 and analogues and derivatives thereof.

Conformational stability of protein based drugs is important for maintaining biological activity and for minimizing irreversible loss of structure due to denaturation and fibrillation. Especially large insulinotropic peptides and proteins are labile with respect to conformational change due to complicated refolding patterns. Also, insulinotropic peptides with a known history of fibrillation, such as GLP-1, are particularly sensitive towards destabilization of tertiary structure (i.e. formation of a molten globular state).

In one aspect, the constituent amino acids of a glucagon-like peptide according to the invention may be selected from the group of the amino acids encoded by the genetic code and they may be natural amino acids which are not encoded by the genetic code, as well as synthetic amino acids. Natural amino acids which are not encoded by the genetic code are e.g. hydroxyproline, γ-carboxyglutamate, ornithine, phosphoserine, D-alanine and D-glutamine. Synthetic amino acids comprise amino acids manufactured by chemical synthesis, i.e. D-isomers of the amino acids encoded by the genetic code such as D-alanine and D-leucine, Aib (α-aminoisobutyric acid), Abu (α-aminobutyric acid), Tle (tert-butylglycine), β-alanine, 3-aminomethyl benzoic acid, anthranilic acid.

In one aspect of the invention, the glucagon-like peptide to be acylated according to the invention is a GLP-1 peptide. In another aspect the GLP-1 peptide is selected from the group consisting of:

[desaminoHis7,Glu22,Arg26,Arg34,Lys37]GLP-1(7-37) amide,
[desaminoHis7,Glu22,Arg26,Arg34,Lys37]GLP-1-(7-37),
[desaminoHis7,Arg34]GLP-1-(7-37),
[Aib8,Glu22,Arg26,Arg34,Lys37]GLP-1-(7-37)amide,
[DesaminoHis7, Glu22 Arg26, Arg 34, Phe(m-CF3)28] GLP-1-(7-37)amide,
[DesaminoHis7,Glu22,Arg26,Arg34]GLP-1-(7-37)-Lys,
[DesaminoHis7,Glu22,Arg26,Arg34]GLP-1-(7-37)-Lys,
[desaminoHis7,Arg26,Arg34,]GLP-1-(7-37)-Lys,
[DesaminoHis7,Glu22,Arg26,Arg34,Lys37]GLP-1-(7-37)amide,
[DesaminoHis7,Arg26,Arg34,Lys37]GLP-1-(7-37) amide,
[DesaminoHis7,Glu22,Arg26,Arg34,Lys37]GLP-1-(7-37),
[DesaminoHis7,Arg26,Arg34,Lys37]GLP-1-(7-37),
[DesaminoHis7,Glu22,Arg26,Glu30,Arg34,Lys37]GLP-1-(7-37),
[Aib8,Lys20,Arg26,Glu30,Thr(O-benzyl)33,]GLP-1-(7-37)amide,
[Aib8,Glu22,Arg26,Lys30]GLP-1-(7-37), [Aib8, Glu22, Arg26,Lys 31]GLP-1-(7-37),
[Aib8,Lys20,Arg26,2-Naphtylalanine28, Glu30,]GLP-1 (7-37)amide,
[Aib8, Glu22, Arg26, Arg34,]GLP-1-(7-37)-Lys,
[Aib8,Lys20,Arg 26,2-Naphtylalanine12, Glu30,]GLP-1-(7-37)amide,
[Aib8,Glu22,Arg26,Lys31,Arg34]GLP-1-(7-37),
[Aib8,Arg34]GLP-1-(7-37),
[Aib8,Arg34]GLP-1-(7-37)-amide,
[Aib8,Lys18,Arg26,Arg34]GLP-1(7-37),
[Aib8,Glu22,Arg26,Arg34,Lys37]GLP-1-(7-37)amide,
[Aib8, Lys 26]GLP-1 (7-37)amide,
[Aib8,Arg34]GLP-1-(7-34),
[Aib8,Arg34]GLP-1-(7-35),
[Aib8,Lys33,Arg34]GLP-1-(7-34),
[Aib8,Arg34]GLP-1-(7-36)amide,
[Aib8,Lys26,Arg34]GLP-1-(7-36)amide,
[Aib8,Glu22,Arg26,Arg34]GLP-1-(7-37)Lys,
[Aib8,Lys20,Glu22,Arg26,Glu30,Pro37]GLP-1-(7-37) amide,
[Aib8,Glu22,Arg26,Arg34,Lys37]GLP-1-(7-37)amide,
[DesaminoHis7,Glu22,Arg26,Arg34,Lys37]GLP-1-(7-37)amide,
[DesaminoHis7,Arg26,Arg34,Lys37]GLP-1-(7-37) amide,
[Aib8,Glu22,Arg26,Glu30,Pro37]GLP-1-(7-37)Lys,
[Aib8,Aib35]GLP-1-(7-37),
Arg34GLP-1-(7-37),
[Aib8,Glu22,Arg26,Glu30,Pro37]GLP-1-((7-37)Lys, and
[Aib8,Arg26,Arg34]GLP-1-(7-37).

In one aspect an acylated glucagon-like peptide is obtained by the method of the invention. In another aspect the acylated glucagon-like peptide obtained by the method of the invention is an acylated GLP-1 peptide. In yet another aspect the acylated GLP-1 peptide is selected from the group consisting of:

N-epsilon26-[2-(2-(2-(2-[2-(2-[4-(15-carboxypentadecanoylamino)-4(S)-carboxybutyrylamino) ethoxy) ethoxy]acetyl)amino)ethoxy)ethoxy)acetyl][Aib8,Arg34] GLP-1-(7-37)peptide, N-epsilon26-[2-(2-(2-(2-[2-(2-[4-(16-carboxyhexadecanoylamino)-4(S)-carboxybutyrylamino) ethoxy)ethoxy] acetyl)amino)ethoxy)ethoxy)acetyl][Aib8,Arg34]GLP-1-(7-37)peptide, N-epsilon26-[2-(2-[2-(2-[2-(2-[4-(17-Carboxyheptadecanoylamino)-4(S)-carboxybutyrylamino]ethoxy)ethoxy] acetylamino)ethoxy]ethoxy)acetyl][Aib8,Arg34]GLP-1-(7-37)peptide, N-epsilon26-[2-(2-[2-(2-[2-(2-[4-(18-Carboxyoctaadecanoylamino)-4(S)-carboxybutyrylamino]ethoxy)ethoxy] acetylamino)ethoxy]ethoxy)acetyl][Aib8,Arg34]GLP-1-(7-37)peptide, N-epsilon26-[2-(2-[2-(2-[2-(2-[4-(19-Carboxynonadecanoylamino)-4(S)-carboxybutyrylamino]ethoxy)ethoxy] acetylamino)ethoxy]ethoxy)acetyl][Aib8,Arg34]GLP-1-(7-37)peptide, N-epsilon26-[2-(2-[2-(2-[2-(2-[4-(20-Carboxeicosanoylamino)-4(S)-carboxybutyrylamino]ethoxy)ethoxy]acetylamino)ethoxy]ethoxy)acetyl][Aib8,Arg34]GLP-1-(7-37) peptide, N-epsilon26-[2-(2-[2-(2-[2-(2-[4-(20-Carboxeicosanoylamino)-4(S)-carboxybutyrylamino]ethoxy)ethoxy]acetylamino)ethoxy]ethoxy)acetyl][Aib8,Arg34]GLP-1-(7-37) peptide, N-epsilon26-[2-(2-[2-(2-[2-(2-[4-(17-Carboxyheptadecanoylamino)-4(R)carboxybutyrylamino]ethoxy)ethoxy] acetylamino)ethoxy]ethoxy)acetyl][Aib8,Arg34]GLP-1-(7-37)peptide, N-epsilon26-[2-(2-[2-(2-[2-(2-[4-(17-Carboxyheptadecanoylamino)-4(S)-carboxypropylamino]ethoxy)ethoxy] acetylamino)ethoxy]ethoxy)acetyl][Aib8,Arg34]GLP-1-(7-37)peptide N-epsilon37-{2-(2-(2-(2-[2-(2-(4-(hexadecanoylamino)-4-carboxybutyrylamino)ethoxy) ethoxy]acetyl)ethoxy) ethoxy)acetyl)}-[desaminoHis7,Glu22,Arg26, Glu30, Arg34,Lys37] (GLP-1-(7-37)amide, N-epsilon37-{2-(2-(2-(2-[2-(2-(4-(hexadecanoylamino)-4-carboxybutyrylamino)ethoxy) ethoxy]acetyl)ethoxy) ethoxy)acetyl)}-[desaminoHis7,Glu22, Arg26,Arg34,Lys 37] (GLP-1-(7-37)amide, N-epsilon37-(2-(2-(2-(2-(2-(2-(2-(2-Octadecanoylamino)ethoxy)ethoxy)acetylamino) ethoxy)ethoxy) acetylamino)ethoxy)ethoxy)acetyl) [desaminoHis7, Glu22,Arg26,Arg34,Lys37] GLP-1 (7-37)amide, N-epsilon36-(2-(2-(2-((2-[2-(2-(17-carboxyheptadecanoylamino)ethoxy)ethoxy]acetylamino)ethoxy)ethoxy) acetyl) [Aib8,Glu22,Arg26,Glu30,Lys36] GLP-1-(7-37) Glu-amide, N-epsilon37-[2-(2-{2-[2-(2-{2-[(S)-4-Carboxy-4-(19-carboxynonadecanoyl amino)butyrylamino]ethoxy}ethoxy) acetylamino]ethoxy}ethoxy)acetyl][DesaminoHis7,Glu22,Arg26,Arg34,Lys37]GLP-1-(7-37), and N-epsilon31-[2-(2-{2-[2-(2-{2-[4-Carboxy-4-(17-carboxyheptadecanoylamino) butyrylamino]ethoxy}ethoxy) acetylamino]ethoxy}ethoxy)acetyl][Aib8,Glu22,Arg26,Lys31]GLP-1-(7-37).

N-epsilon26-[2-(2-{2-[2-(2-{2-[2-(2-{2-[4-Carboxy-4-(17-carboxy-heptadecanoylamino)butyrylamino] ethoxy}ethoxy)acetylamino]ethoxy}ethoxy) actylamino] ethoxy}ethoxy)-acetyl][Aib8,Arg34]GLP-1-(7-37) peptide GLP-1-(7-37) peptide, N-epsilon26-[2-(2-{2-[(S)-4-Carboxy-4-(17-carboxyheptadecanoylamino) butyrylamino]ethoxy}ethoxy)acetyl] Aib8,Arg34] GLP-1(7-37)peptide The present invention is also particularly suited for the acylation of insulin and analogues thereof.

In one aspect of the invention, the insulin to be acylated according to the invention is human insulin or a human insulin analogue. A human insulin analogue according to the invention is human insulin wherein one or more amino acids have been substituted by other amino acid residue(s), inserted, deleted from the insulin and/or added compared to human insulin. In one aspect between 1 and 5, 1 and 4, 1 and 3 or between 1 and 2 amino acids have been substituted, inserted, deleted and/or added relative to the amino acid sequence of human insulin.

Examples of insulin analogues according to the invention are such wherein Pro in position 28 of the B chain is mutated with Asp, Lys, Leu, Val, or Ala and/or Lys at position B29 is mutated with Pro, Glu or Asp. Furthermore, Asn at position B3 may be mutated with Thr, Lys, Gln, Glu or Asp. The amino acid residue in position A21 may be mutated with Gly. The amino acid in position B1 may be mutated with Glu. The amino acid in position B16 may be mutated with Glu or His. Further examples of insulin analogues are the deletion analogues e.g. analogues where the B30 amino acid in human insulin has been deleted (des(B30) human insulin), insulin analogues wherein the B1 amino acid in human insulin has been deleted (des(B1) human insulin), des(B28-B30) human insulin and des(B27) human insulin. Insulin analogues wherein the A-chain and/or the B-chain have an N-terminal extension and insulin analogues wherein the A-chain and/or the B-chain have a C-terminal extension such as with two arginine residues added to the C-terminal of the B-chain are also examples of insulin analogues. Further examples are insulin analogues comprising combinations of the mentioned mutations. Insulin analogues wherein the amino acid in position A14 is Asn, Gln, Glu, Arg, Asp, Gly or His, the amino acid in position B25 is His and which optionally further comprises one or more additional mutations are further examples of insulin analogues. Insulin analogues of human insulin wherein the amino acid residue in position A21 is Gly and wherein the insulin analogue is further extended in the C-terminal with two arginine residues are also examples of insulin analogues In one aspect the insulin is selected from the group consisting of:
Human insulin,
DesB30 human insulin,
AspB28 human insulin,
AspB28,desB30 human insulin,
LysB3,GluB29 human insulin,
LysB28,ProB29 human insulin,
GlyA21,ArgB31,ArgB32 human insulin,
GluA14,HisB25 human insulin,
HisA14,HisB25 human insulin,
GluA14,HisB25,desB30 human insulin,
HisA14, HisB25,desB30 human insulin,
GluA14,HisB25,desB27,desB28,desB29,desB30 human insulin,
GluA14,HisB25,GluB27,desB30 human insulin,
GluA14,HisB16,HisB25,desB30 human insulin,
HisA14,HisB16,HisB25,desB30 human insulin,
HisA8,GluA14,HisB25,GluB27,desB30 human insulin,
GluA14,HisB25,desB27,desB30 human insulin,
GluA14,GlyA21,HisB25,desB30 human insulin,
GluA14,HisB25,LysB27,desB28,desB29,desB30 human insulin,
HisA8,GluA14,GluB1,GluB16,HisB25,GluB27,desB30 human insulin, and
HisA8,GluA14,GluB16,HisB25,desB30 human insulin.

In one aspect an acylated insulin peptide is obtained by the method of the invention. In another aspect the acylated insulin peptide obtained by the method of the invention is selected from the group consisting of:
A14E, B25H, B29K(N$^\epsilon$Octadecanedioyl-gGlu-[2-(2-{2-[2-(2-aminoethoxy)ethoxy]-acetylamino}ethoxy)ethoxy] acetyl)), desB30 human insulin (alternative name: A14E, B25H, B29K(N$^\epsilon$Octadecanedioyl-gGlu-OEG-OEG), desB30 human insulin), A14E, B16H, B25H, B29K(MEicosanedioyl-gGlu-[2-(2-{2-[2-(2-aminoethoxy)ethoxy]acetylamino}ethoxy)ethoxy] acetyl)), desB30 human insulin (alternative name: A14E, B16H, B25H, B29K(N$^\epsilon$Eicosanedioyl-gGlu-OEG-OEG), desB30 human insulin), A14E, B25H, B29K(N$^\epsilon$Eicosanedioyl-gGlu-[2-(2-{2-[2-(2-aminoethoxy)ethoxy]-acetylamino}ethoxy)ethoxy] acetyl)), desB27, desB30 human insulin (alternative name: A14E, B25H, B29K(N$^\epsilon$Eicosanedioyl-gGlu-OEG-OEG), desB27, desB30 human insulin), A14E, B25H, B27K(N$^\epsilon$Octadecanedioyl-gGlu-[2-(2-{2-[2-(2-aminoethoxy)ethoxy]-acetylamino}ethoxy)ethoxy] acetyl)), desB28, desB29, desB30 human insulin (alternative name: A14E, B25H, B27K(N$^\epsilon$Octadecanedioyl-gGlu-OEG-OEG), desB28, desB29, desB30 human insulin), A14E, B25H, B27E, B29K(N$^\epsilon$Eicosanedioyl-gGlu-[2-(2-{2-[2-(2-aminoethoxy)ethoxy]-acetylamino}ethoxy) ethoxy]acetyl)), desB30 human insulin (alternative name: A14E, B25H, B27E, B29K(N$^\epsilon$Eicosanedioyl-gGlu-OEG-OEG), desB30 human insulin), A14E, B25H, desB27, B29K(N$^\epsilon$Octadecanedioyl-gGlu-[2-(2-{2-[2-(2-aminoethoxy)ethoxy]acetylamino}ethoxy) ethoxy]acetyl)), desB30 human insulin (alternative name: A14E, B25H, desB27, B29K(N$^\epsilon$Octadecanedioyl-gGlu-OEG-OEG), desB30 human insulin), A14E, B25H, B29K((N$^\epsilon$Eicosanedioyl-gGlu-[2-(2-{2-[2-(2-aminoethoxy)ethoxy]-acetylamino}ethoxy)ethoxy] acetyl)), desB30 human insulin (alternative name: A14E, B25H, B29K((N$^\epsilon$Eicosanedioyl-gGlu-OEG-OEG), desB30 human insulin), A14E, B16H, B25H, B29K(N$^\epsilon$Octadecanedioyl-gGlu-[2-(2-{2-[2-(2-aminoethoxy)ethoxy]acetylamino}ethoxy) ethoxy]acetyl)), desB30 human insulin (Alternative name: A14E, B16H, B25H, B29K(N$^\epsilon$Octadecanedioyl-gGlu-OEG-OEG), desB30 human insulin), and A14E, A21 G, B25H, B29K(N$^\epsilon$Octadecanedioyl-gGlu-[2-(2-{2-[2-(2-aminoethoxy)ethoxy]acetylamino}ethoxy) ethoxy]acetyl)), desB30 human insulin (alternative name: A14E, A21G, B25H, B29K(N$^\epsilon$Octadecanedioyl-gGlu-OEG-OEG), desB30 human insulin).

The production of peptides and proteins is well known in the art. Peptides or proteins may for instance be produced by classical peptide synthesis, e.g. solid phase peptide synthesis using t-Boc or Fmoc chemistry or other well established techniques, see e.g. Greene and Wuts, "Protective Groups in Organic Synthesis", John Wiley & Sons, 1999, "Organic Synthesis on solid Phase", Florencio Zaragoza Dorwald, Wiley-VCH Verlag GmbH, D-69469 Weinheim, 2000, "Novabiochem Catalog", Merck Biosciences 2006/2007 and "Fmoc Solid Phase Peptide Synthesis", Edited by W.C. Chan and P.D. White, Oxford University Press, 2000, ISBN 0-19-963724-5. The peptides or proteins may also be produced by a method which comprises culturing a host cell containing a DNA sequence encoding the peptide or protein and capable of expressing the peptide or protein in a suitable nutrient medium under conditions permitting the expression of the peptide or protein. For peptides or proteins comprising non-natural amino acid residues, the recombinant cell should be modified such that the non-natural amino acids are incorporated into the peptide or protein, for instance by use of tRNA mutants.

The following is a non-limiting list of aspects further comprised by the invention:
1. A method for selectively acylating one amino group in a peptide or protein which has two or more reactive nucleophilic functional groups, the method comprising:
   a) reacting in an aqueous media a peptide or protein having at least two reactive nucleophilic functional groups with an acylating agent of the general formula I

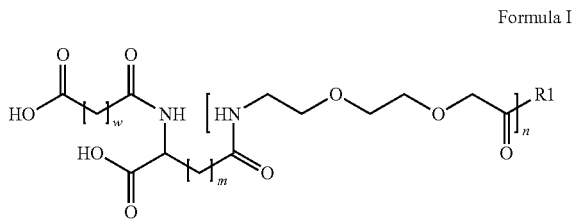

Formula I wherein
n is 0-4
m is 1-2
w is 4-20
R1 is a leaving group which when reacting said acylating agent with a free amine facilitates the formation of an amide bond between the carbonyl group attached to R1 and said amine,
wherein pH in the aqueous media is between from pH 8.0 to pH 14; and
   b) isolating the N-acylated peptide or protein,
wherein an N-acylated peptide or protein is obtained comprising at least one reactive nucleophilic functional group which is not acylated or only partially acylated.
2. A method for selectively acylating one amino group in a peptide or protein which has two or more reactive nucleophilic functional groups according to aspect 1, wherein said reactive nucleophilic functional group is selected from the group consisting of: hydroxyl-groups, thiol groups and amino-groups.
3. A method for selectively acylating one amino group in a peptide or protein which has two or more reactive nucleophilic functional groups according to aspect 1 or 2, wherein said reactive nucleophilic functional groups are amino-groups.
4. A method for selectively acylating one amino group in a peptide or protein which has two or more reactive nucleophilic functional groups according to any one of aspects 1-3, wherein an N-acylated peptide or protein is obtained wherein the acylation is in the ε-position of a lysine and at least one free amino group of the peptide or protein is not acylated.
5. A method for selectively acylating one amino group in a peptide or protein which has two or more reactive nucleophilic functional groups according to any one of aspects 1-4, wherein R1 in formula I together with the carbonyl to which $R^1$ is attached designate an ester.
6. A method for selectively acylating one amino group in a peptide or protein which has two or more reactive nucleophilic functional groups according to any one of aspects 1-4, wherein R1 in formula I together with the carbonyl to which $R^1$ is attached designate an activated ester.
7. A method for selectively acylating one amino group in a peptide or reactive nucleophilic functional groups according to any one of aspects 1-4, wherein R1 in formula I together with the carbonyl to which $R^1$ is attached designate an activated N-hydroxy imide ester.
8. A method for selectively acylating one amino group in a peptide or protein which has two or more reactive nucleophilic functional groups according to any one of the preceding aspects, wherein n is 1-5, alternatively 1-2, 1-3 or 1-4, alternatively 2.
9. A method for selectively acylating one amino group in a peptide or protein which has two or more reactive nucleophilic functional groups according to any one of the preceding aspects, wherein m is 1-2, alternatively 2.
10. A method for selectively acylating one amino group in a peptide or protein which has two or more reactive nucleophilic functional groups according to any one the preceding aspects, wherein w is 4-20, alternatively 10-20, alternatively 14-18, alternatively 14, alternatively 16 or alternatively 18.
11. A method for selectively acylating one amino group in a peptide or protein which has two or more reactive nucleophilic functional groups according to any one of the preceding aspects, wherein the pH of the aqueous reaction mixture is between pH 9 and pH 13.
12. A method for selectively acylating one amino group in a peptide or protein which has two or more reactive nucleophilic functional groups according to any one of the preceding aspects, wherein the pH of the aqueous reaction mixture is between pH 10 and pH 12.
13. A method for selectively acylating one amino group in a peptide or protein which has two or more reactive nucleophilic functional groups according to any one of the preceding aspects, wherein the pH of the aqueous reaction mixture is between pH 10.5 and pH 11.5.
14. A method for selectively acylating one amino group in a peptide or protein which has two or more reactive nucleophilic functional groups according to any one of the preceding aspects, wherein the pH of the aqueous reaction mixture is between pH 11 and pH 12.
15. A method for selectively acylating one amino group in a peptide or protein which has two or more reactive nucleophilic functional groups according to any one of the preceding aspects, wherein the pH of the aqueous reaction mixture is between pH 11.5 and pH 12.
16. A method for selectively acylating one amino group in a peptide or protein which has two or more reactive nucleophilic functional groups according to any one of the preceding aspects, wherein the pH of the aqueous reaction mixture is about pH 11.5.
17. A method for selectively acylating one amino group in a peptide or protein which has two or more reactive nucleophilic functional groups according to any one of the preceding aspects, wherein the pH of the aqueous reaction mixture is between pH 11 and 12, such as between pH 11.0 and 11.5 or between pH 11.0 and 11.3.
18. A method for selectively acylating one amino group in a peptide or protein which has two or more reactive nucleophilic functional groups according to any one of the preceding aspects, wherein the pH of the aqueous reaction mixture is about pH 11.3.
19. A method for selectively acylating one amino group in a peptide or protein which has two or more reactive nucleophilic functional groups according to any one of the preceding aspects, wherein the temperature of the reaction mixture during the acylation procedure is between −5° C. and 50° C. such as between 0° C. and 50° C.
20. A method for selectively acylating one amino group in a peptide or protein which has two or more reactive nucleophilic functional groups according to any one of the preceding aspects, wherein the temperature of the reaction mixture during the acylation procedure is between 10° C. and 30° C. such as about 20° C. or r.t.

21. A method for selectively acylating one amino group in a peptide or protein which has two or more reactive nucleophilic functional groups according to any one of the preceding aspects, wherein the temperature of the reaction mixture during the acylation procedure is between 0° C. and 5° C., such as between 2 and 5° C.

22. A method for selectively acylating one amino group in a peptide or protein which has two or more reactive nucleophilic functional groups according to any one of the preceding aspects, wherein the acylation reagent is added with stirring or agitation to the reaction mixture over a period of between 0 min and 480 min.

23. A method for selectively acylating one amino group in a peptide or protein which has two or more reactive nucleophilic functional groups according to any one of the preceding aspects, wherein the reagent is added over a period of between 30 and 60 minutes.

24. A method for selectively acylating one amino group in a peptide or protein which has two or more reactive nucleophilic functional groups according to any one of the preceding aspects, wherein the acylation mixture is left for reaction for between 0 and 24 hours after addition of the acylation reagent.

25. A method for selectively acylating one amino group in a peptide or protein which has two or more reactive nucleophilic functional groups according to any one of the preceding aspects, wherein the reaction is stopped by adjusting the pH to pH 6.5-9.0, such as to e.g. pH 7.5-8.0, immediately after addition of the acylation reagent.

26. A method for selectively acylating one amino group in a peptide or protein which has two or more reactive nucleophilic functional groups according to any one of the preceding aspects, wherein the acylation mixture is left for reaction for between 30 and 60 minutes after addition of the acylation reagent.

27. A method for selectively acylating one amino group in a peptide or protein which has two or more reactive nucleophilic functional groups according to any one of the preceding aspects, wherein the peptide or protein is present in the reaction mixture in a concentration of at least 5.0 mg/ml.

28. A method for selectively acylating one amino group in a peptide or protein which has two or more reactive nucleophilic functional groups according to any one of the preceding aspects, wherein the concentration of the protein or peptide is between 10.0 mg/ml and 20.0 mg/ml.

29. A method for selectively acylating one amino group in a peptide or protein which has two or more reactive nucleophilic functional groups according to any one of the preceding aspects, wherein the concentration of the protein or peptide is approximately 12.5 mg/ml.

30. A method for selectively acylating one amino group in a peptide or protein which has two or more reactive nucleophilic functional groups according to any one of the preceding aspects, wherein the concentration of the protein or peptide is approximately 20 mg/ml.

31. A method for selectively acylating one amino group in a peptide or protein which has two or more reactive nucleophilic functional groups according to any one of the preceding aspects, wherein the reaction mixture comprises a buffer.

32. A method for selectively acylating one amino group in a peptide or protein which has two or more reactive nucleophilic functional groups according to aspect 31, wherein the reaction mixture comprises a buffer which is selected from the group consisting of: Phosphate buffer, Sodium carbonate buffer, Bicine buffer (N,N-Bis(2-hydroxyethyl)glycine buffer), HEPPS buffer (3-[4-(2-Hydroxyethyl)-1-piperazinyl]propanesulfonic acid buffer), HEPES buffer (4-(2-Hydroxyethyl)-1-piperazineethanesulfonic acid buffer), MOPS buffer (3-(NMorpholino)propanesulfonic acid buffer) or TEA buffer (Triethylamine buffer).

33. A method for selectively acylating one amino group in a peptide or protein which has two or more reactive nucleophilic functional groups according to any one of the preceding aspects, wherein the reaction mixture comprises a buffer which is a Phosphate buffer.

34. A method for selectively acylating one amino group in a peptide or protein which has two or more reactive nucleophilic functional groups according to any one of the preceding aspects, wherein the acylation reagent is added to the solution as a solid.

35. A method for selectively acylating one amino group in a peptide or protein which has two or more reactive nucleophilic functional groups according to any one of the preceding aspects, wherein the acylation reagent is added in a solution comprising the acylation agent dissolved in an inert solvent.

36. A method for selectively acylating one amino group in a peptide or protein which has two or more reactive nucleophilic functional groups according to any one of the preceding aspects, wherein the inert solvent is selected from the group consisting of N-methylpyrrolidinone, N,N-dimetylformamide and acetonitril.

37. A method for selectively acylating one amino group in a peptide or protein which has two or more reactive nucleophilic functional groups according to any one of the preceding aspects, wherein the acylation reagent is added to the reaction mixture in a concentration which is between 10 mg/ml and 250 mg/ml.

38. A method for selectively acylating one amino group in a peptide or protein which has two or more reactive nucleophilic functional groups according to any one of the preceding aspects, wherein the reaction in step (a) is performed using the protein and the acylating agent of the formula I in a 1:1 to 1:5 molar ratio.

39. A method for selectively acylating one amino group in a peptide or protein which has two or more reactive nucleophilic functional groups according to any one of the preceding aspects, wherein the peptide or protein is pre-dissolved in an aqueous solution at −10 to 30° C. and the pH is adjusted to the desired level using an alkalimetal hydroxide, an alkali carbonate or a tertiary amine base before the acylating agent is added.

40. A method for selectively acylating one amino group in a peptide or protein which has two or more reactive nucleophilic functional groups according to any one of the preceding aspects, wherein the peptide or protein to be acylated is a peptide or protein which is suitable for treating diabetes.

41. A method for selectively acylating one amino group in a peptide or protein which has two or more reactive nucleophilic functional groups according to any one of the preceding aspects, wherein the peptide or protein to be acylated is a peptide or protein which is suitable for treating obesity.

42. A method for selectively acylating one amino group in a peptide or protein which has two or more reactive nucleophilic functional groups according to any one of the preceding aspects, wherein the peptide or protein to be acylated is a glucagon-like peptide or an insulin.

43. A method for selectively acylating one amino group in a peptide or protein which has two or more reactive nucleophilic functional groups according to aspect 42, wherein the peptide or protein to be acylated is a glucagon-like peptide.

44. A method for selectively acylating one amino group in a peptide or protein which has two or more reactive nucleophilic functional groups according to aspect 43, wherein the glucagon-like peptide is dipeptidyl aminopeptidase IV protected.

45. A method for selectively acylating one amino group in a peptide or protein which has two or more reactive nucleophilic functional groups according to any one of aspects 43 or 44, wherein the glucagon-like peptide is selected from the group consisting of glucagon peptides, GLP-1 peptides, GLP-2 peptides, exendin-3 peptides and exendin-4 peptides.

46. A method for selectively acylating one amino group in a peptide or protein which has two or more reactive nucleophilic functional groups according to aspect 45, wherein the glucagon-like peptide is a GLP-1 peptide.

47. A method for selectively acylating one amino group in a peptide or protein which has two or more reactive nucleophilic functional groups according to aspect 46, wherein the GLP-1 peptide is selected from the group consisting of: GLP-1 (7-37), GLP-1(7-36) amide, Gly8-GLP-1(7-37), Val8-GLP-1(7-36)-amide and [Val8Asp22]-GLP-1(7-37), [desaminoHis7,Glu22,Arg26,Arg34,Lys37]GLP-1(7-37) amide, [desaminoHis7,Glu22,Arg26,Arg34,Lys37]GLP-1-(7-37), [desaminoHis7,Arg34]GLP-1-(7-37), [Aib8,Glu22, Arg26,Arg34,Lys37]GLP-1-(7-37)amide, [DesaminoHis7, Glu22 Arg26, Arg 34, Phe(m-CF3)28]GLP-1-(7-37)amide, [DesaminoHis7,Glu22,Arg26,Arg34]GLP-1-(7-37)-Lys, [DesaminoHis7,Glu22,Arg26,Arg34]GLP-1-(7-37)-Lys, [desaminoHis7,Arg26,Arg34,]GLP-1-(7-37)-Lys, [DesaminoHis7,Glu22,Arg26,Arg34,Lys37]GLP-1-(7-37)amide, [DesaminoHis7,Arg26,Arg34,Lys37]GLP-1-(7-37)amide, [DesaminoHis7,Glu22,Arg26,Arg34,Lys37]GLP-1-(7-37), [DesaminoHis7,Arg26,Arg34,Lys37]GLP-1-(7-37), [DesaminoHis7,Glu22,Arg26,Glu30,Arg34,Lys37]GLP-1-(7-37), [Aib8,Lys20,Arg26,Glu30,Thr(O-benzyl)33,]GLP-1-(7-37) amide, [Aib8,Glu22,Arg26,Lys30]GLP-1-(7-37), [Aib8, Glu22, Arg26,Lys 31]GLP-1-(7-37), [Aib8,Lys20,Arg26,2-Naphtylalanine28, Glu30,]GLP-1 (7-37)amide, [Aib8, Glu22, Arg26, Arg34,]GLP-1-(7-37)-Lys, [Aib8,Lys20,Arg 26, 2-Naphtylalanine12, Glu30,]GLP-1-(7-37)amide, [Aib8, Glu22,Arg26,Lys31,Arg34]GLP-1-(7-37), [Aib8,Arg34] GLP-1-(7-37), [Aib8,Arg34]GLP-1-(7-37)-amide, [Aib8, Lys18,Arg26,Arg34]GLP-1(7-37), [Aib8,Glu22,Arg26, Arg34,Lys37]GLP-1-(7-37)amide, [Aib8, Lys 26] GLP-1 (7-37)amide, [Aib8,Arg34]GLP-1-(7-34), [Aib8,Arg34] GLP-1-(7-35), [Aib8,Lys33,Arg34]GLP-1-(7-34), [Aib8, Arg34]GLP-1-(7-36)amide, [Aib8,Lys26,Arg34]GLP-1-(7-36)amide, [Aib8,Glu22,Arg26,Arg34]GLP-1-(7-37)Lys, [Aib8,Lys20,Glu22,Arg26,Glu30,Pro37]GLP-1-(7-37) amide, [Aib8,Glu22,Arg26,Arg34,Lys37]GLP-1-(7-37) amide, [DesaminoHis7,Glu22,Arg26,Arg34,Lys37]GLP-1-(7-37)amide, [DesaminoHis7,Arg26,Arg34,Lys37]GLP-1-(7-37)amide,
 [Aib8,Glu22,Arg26,Glu30,Pro37]GLP-1-(7-37)Lys, [Aib8,Aib35]GLP-1-(7-37), Arg34GLP-1-(7-37), [Aib8, Glu22,Arg26,Glu30,Pro37]GLP-1-((7-37)Lys, and [Aib8, Arg26,Arg34]GLP-1-(7-37).

48. A method for selectively acylating one amino group in a peptide or protein which has two or more reactive nucleophilic functional groups according to aspect 42, wherein the peptide or protein to be acylated is an insulin.

49. A method for selectively acylating one amino group in a peptide or protein which has two or more reactive nucleophilic functional groups according to aspect 48, wherein the insulin is human insulin or a human insulin analogue, wherein a human insulin analogue is human insulin wherein between 1 and 5 amino acids have been substituted by other amino acid residue(s), inserted, deleted from the insulin and/or added compared to human insulin.

50. A method for selectively acylating one amino group in a peptide or protein which has two or more reactive nucleophilic functional groups according to aspect 49, wherein the insulin is selected from the group consisting of:

Human insulin, DesB30 human insulin, AspB28 human insulin, AspB28,desB30 human insulin, LysB3,GluB29 human insulin, LysB28,ProB29 human insulin, GlyA21,ArgB31, ArgB32 human insulin, GluA14,HisB25 human insulin, HisA14,HisB25 human insulin, GluA14,HisB25,desB30 human insulin, HisA14, HisB25,desB30 human insulin, GluA14,HisB25,desB27,desB28,desB29,desB30 human insulin, GluA14,HisB25,GluB27,desB30 human insulin, GluA14,HisB16,HisB25,desB30 human insulin, HisA14, HisB16,HisB25,desB30 human insulin, HisA8,GluA14, HisB25,GluB27,desB30 human insulin, HisA8,GluA14, GluB1,GluB16,HisB25,GluB27,desB30 human insulin, and HisA8,GluA14,GluB16,HisB25,desB30 human insulin.

51. A method for selectively acylating one amino group in a peptide or protein which has two or more reactive nucleophilic functional groups according to any one of the preceding aspects, wherein an N-acylated peptide or protein is obtained comprising at least one free amino group which is not acylated.

52. A method for selectively acylating one amino group in a peptide or protein according to any one of the preceding aspects, wherein the peptide or protein to be acylated has 2 free amino groups and only one amino group is acylated.

EXAMPLES

Example 1

Preparation of 1,18-Octadecanedioic Acid Mono Benzyl Ester

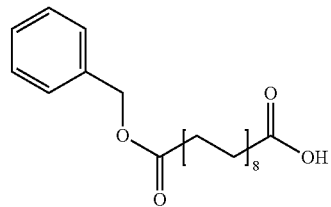

A solution of 1,18-octadecanedioic acid (75 g, 0.24 mol), p-toluene sulfonic acid mono hydrate (2.27 g, 11.9 mmol) and benzyl alcohol (20.7 g, 0.19 mol) in toluene (2.75 L) was heated to reflux for 3 hr. Water was removed by azeotropic distillation during reflux. Celite (25 g) was added and the mixture was cooled to 40° C. and stirred for an additional hour. The mixture was purified by plug filtration through silica using toluene as mobile phase. Fractions containing 1,18-octadecanedioic acid mono benzyl ester was collected and the volume was reduced by vacuum distillation at 75° C. The solution was cooled to 50° C., heptane was added, and the mixture was cooled to 35° C. Upon crystallisation additional heptane was added over a period of 15 min. and finally the mixture was cooled to 10° C. for an additional hour. The product was collected by filtration, washed with heptane and dried in vacuum. Yield of 1,18-octadecanedioic acid mono benzyl ester was 34 g (35%).

Example 2

Preparation of Benzyl 18-[(2,5-dioxo-1-pyrrolidinyl)oxy]-18-oxooctadecanoate

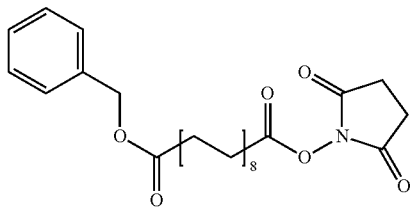

1,18-octadecanedioic acid mono benzyl ester (120 g, 0.3 mol), N-hydroxysuccinimide (41 g, 0.36 mol) and N,N-dicyclohexylcarbodiimide (74 g, 0.36 mol) were dissolved in NMP (1200 ml) and heated to 60° C. for 2.5 hr. The reaction mixture was cooled to 25° C. and the precipitate was removed by filtration and washed with water (4.7 L). The crude precipitate was recystallised from 2-propanol (1250 ml), affording benzyl 18-[(2,5-dioxo-1-pyrrolidinyl)oxy]-18-oxooctadecanoate. Yield 138 g (92%).

Example 3

Preparation of Benzyl 18-({(1S)-1-[(benzyloxy)carbonyl]-4-[(2,5-dioxo-1-pyrrolidinyl)oxy]-4-oxobutyl}amino)-18-oxooctadecanoate

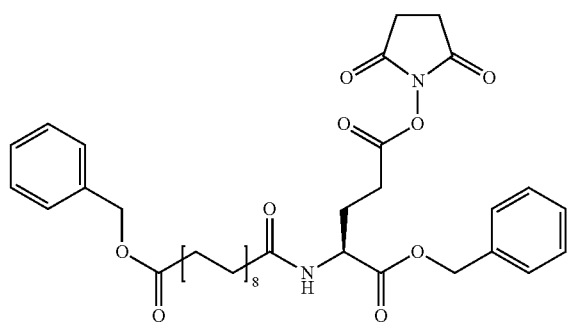

Benzyl 18-[(2,5-dioxo-1-pyrrolidinyl)oxy]-18-oxooctadecanoate (30 g, 60 mmol) and L-glutamic acid alpha-benzyl ester (15 g, 62.8 mmol) were dissolved in NMP and heated at 50° C. for 4 hr. Water (700 ml), KHSO$_4$ (100 ml, 0.5 M aq.) and ethylacetate (220 ml) was added at 25° C. The organic phase was washed twice with KHSO$_4$ (aq, 150 ml, 0.17 M), and evaporated in vacuo. The mixture was redissolved in NMP (225 ml), N-hydroxysuccinimide (11 g, 95.7 mmol) and N,N-dicyclohexylcarbodiimide (16 g, 77.7 mmol) were added and the solution was stirred for 16 hr. The precipitate was removed by filtration and washed with water (1 L). The crude precipitate was recystallised from 2-propanol, affording benzyl 18-[(2,5-dioxo-1-pyrrolidinyl)oxy]-18-oxooctadecanoate. Yield 32.7 g (76%).

Example 4

Preparation of (22S)-22-carboxy-1-[(2,5-dioxo-1-pyrrolidinyl)oxy]-1,10,19,24-tetraoxo-3,6,12,15-tetraoxa-9,18,23-triazahentetracontan-41-oic acid (compound 1)

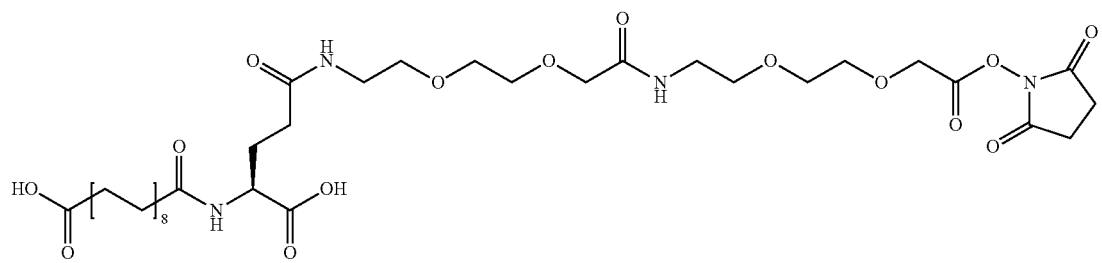

Compound 1

Benzyl 18-[(2,5-dioxo-1-pyrrolidinyl)oxy]-18-oxooctadecanoate (100 g, 138.7 mmol) and 17-amino-10-oxo-3,6,12,15-tetraoxa-9-azaheptadecan-1-oic acid (44.9 g, 145.6 mmol) were suspended in aceonitrilacetonitril (10. Triethylamine (20.8 ml, 150 mmol) was added and the mixture was stirred for 16 hr. Water (3 L), KHSO$_4$ (aq. 0.5M, 10, and ethylacetate (1 L) was added. The organic phase was evaporated in vacuo, and coevaporated twice with toluene (2×300 ml). N-Hydroxysuccinimide (17.6 g, 153 mmol), 1-ethyl-3-(3'-dimethylaminopropyl)carbodiimide hydrochloride (31.9 g, 166.5 mmol) and 2-propanol (1 L) were added and the solution was stirred for 16 hr. Dichloromethane (1 L), water (3 L) and KHSO$_4$ (aq. 0.5M, 1 L) were added. The organic phase was collected, dried over MgSO$_4$, filtered, evaporated in vacuo and coevaporated twice with toluene (2×300 ml). 2-Propanol (1300 ml) and Pd/C (14 g) was added and the mixture was hydrogenated for 2 hr. The mixture was heated to 39° C. and filtered. The solution is was cooled, and the precipitate was collected by filtration. Yield 100 g (87%).

Example 5

Analytical HPLC

The following HPLC gradient was used for analysing the obtained acylation products Buffer A: 1800 ml Milli-Q water, 200 ml acetonitril and 2 ml H3PO4

Buffer B: 1800 ml acetonitril, 200 ml Milli-Q water and 2 ml H3PO4

Column: Jupiter 4μ Proteo 90A kolonne fra Phenomenex.

Gradient is given in table 5.1

TABLE 5.1

| Tid(min) | Buffer A | Buffer B | Flow |
|---|---|---|---|
| 0.0 | 80% | 20% | 1.0 ml |
| 5.0 | 60% | 40% | 1.0 ml |
| 20.0 | 25% | 75% | 1.0 ml |
| 21.0 | 0% | 100% | 1.0 ml |
| 25.0 | 0% | 100% | 1.0 ml |
| 26.0 | 80% | 20% | 1.0 ml |
| 33.0 | 80% | 20% | 1.0 ml |

Example 6

Acylation of [Aib$^8$, Arg$^{34}$]GLP-1(7-37) with 22-carboxy-1-[(2,5-dioxo-1-pyrrolidinyl)oxy]-1,10,19,24-tetraoxo-3,6,12,15-tetraoxa-9,18,23-triazahentetracontan-41-oic acid (Compound 1)

General Experimental:

In a round bottle flask equipped with a magnetic stirring bar was added the peptide intermediate [Aib$^8$, Arg$^{34}$]GLP-1(7-37) peptide and MilliQ water resulting in a suspension with a concentration given in table 6.1. The round bottle flask was submerged into a large (2 L) container of water, which was adjusted to a fixed temperature of 20 degrees by a Julabo HL-4 Heating Circulator. A Radiometer PHM290 pH-stat controller was calibrated with 2 individual IUPAC standard buffers (pH 9.18 and 12.45) and connected to a Radiometer ABU901 autoburette (2 ml) equipped with a solution of an aqueous NaOH (0.1M). The electrode was dipped into the mixture (typically pH=2.5). 4M NaOH was added to a fixed pH setpoint (see table 6.1 for pH details). The acylating agent (compound 1) was evaluated by 1H-NMR with an internal standard prior to use. A syringe pump was equipped with a syringe containing a solution of 10% w/w acylating agent in NMP (app. 3 eq. relative to peptide intermediate) and continuously added dropwise to the solution of the peptide intermediate over 60 min (i.e. app. 1 eq. of acylating agent/20 min). pH was fixed to the setpoint by the PHM290 controller. IPC's were taken over suitable intervals and analysed by HPLC (260 nm, example 5), % area are given in table 6.1.

TABLE 6.1

| pH | Temp. | Conc. peptide | eq. acylating agent | Lys-26 acylated | Nα- and Lys-26 diacylated |
|---|---|---|---|---|---|
| 10.0 | 20° C. | 12.5 g/L | 1.44 | 87.9% | 6.3% |
| 10.5 | 20° C. | 12.5 g/L | 1.44 | 92.0% | 4.3% |
| 10.75 | 20° C. | 12.5 g/L | 1.44 | 92.7% | 3.6% |
| 10.9* | 10° C. | 12.5 g/L | 1.53 | 91.8% | 2.44% |
| 11.0 | 20° C. | 12.5 g/L | 1.72 | 93.3% | 3.4% |
| 11.25 | 20° C. | 5.0 g/L | 2.30 | 95.9% | 1.7% |
| 11.25* | 10° C. | 12.5 g/L | 2.13 | 91.9% | 3.8% |
| 11.25 | 20° C. | 12.5 g/L | 1.72 | 94.3% | 2.3% |
| 11.25* | 30° C. | 12.5 g/L | 2.14 | 91.9% | 3.8% |
| 11.25 | 20° C. | 25.0 g/L | 1.65 | 93.7% | 3.2% |
| 11.5 | 20° C. | 12.5 g/L | 2.01 | 94.2% | 2% |
| 11.5* | 30° C. | 12.5 g/L | 2.76 | 93.7% | 2.6% |
| 12.0 | 20° C. | 12.5 g/L | 4.37 | 90.5% | 1.2% |

*pH was measured at 20° C.

Example 7

Acylation of [Aib$^8$, Arg$^{34}$]GLP-1(7-37) with 22-carboxy-1-[(2,5-dioxo-1-pyrrolidinyl)oxy]-1,10,19,24-tetraoxo-3,6,12,15-tetraoxa-9,18,23-triazahentetracontan-41-oic acid (Compound 2)

[Aib$^8$, Arg$^{34}$]GLP-1(7-37) peptide (10.0 g, 2.94 mmol) was suspended in water to a conc. of app. 15 g/I, pH was adjusted to 11.25 with NaOH (aq. 1 M), and water was added to a final peptide conc. of app. 12.5 g/L. Acylating agent 22-carboxy-1-[(2,5-dioxo-1-pyrrolidinyl)oxy]-1,10,19,24-tetraoxo-3,6,12,15-tetraoxa-9,18,23-triazahentetracontan-41-oic acid (compound 1, 3.7 g, 4.41 mmol) was dissolved in NMP (10% w/v) and added stepwise to the aqueous solution. pH was kept constant between 11.1 and 11.3 by continuous addition of NaOH (aq., 1M) during reaction. Samples were withdrawn and analyzed by RP HPLC (according to the gradient of example 5) during the reaction. After the addition of acylating agent had ended, the reaction mixture was stirred for an additional 60 min. before pH was adjusted to app. 7.5 by addition of sulphuric acid (aq., 1M). HPLC (260 nm, example 5), area % 92.6%, yield by assay titration with standard, 91.5%.

Example 8

Acylation of [Aib$^8$, Arg$^{34}$]GLP-1(7-37) with 22-carboxy-1-[(2,5-dioxo-1-pyrrolidinyl)oxy]-1,10,19,24-tetraoxo-3,6,12,15-tetraoxa-9,18,23-triazahentetracontan-41-oic acid (Compound 1)

Experimental:

To a round bottle flask equipped with a magnetic stirring bar was added the peptide intermediate [Aib$^8$, Arg$^{34}$]GLP-1 (7-37) peptide (234 mg, 0.069 mmol) and MilliQ water (18.3 ml) resulting in a suspension. A pH-meter was calibrated with 2 individual IUPAC standard buffers (pH 9.18 and 12.45) and submerged into the solution. Et$_3$N was added until pH 10. Compound 1 was evaluated by 1H-NMR with an internal standard, prior to use. A syringe pump was equipped with a syringe containing a solution of 10% w/w acylating agent (compound 1, 120 mg, 0.144 mmol) in NMP and the solution was continuously added dropwise to the solution of the peptide intermediate. pH was maintained between 9.8 and 10.4 during addition. pH was adjusted to 7.2 with AcOH and analysed by HPLC (260 nm) % area are given in the table below.

| pH | Temp. | Conc. peptide | eq. acylating agent | Lys-26 acylated | Nα- and Lys-26 diacylated |
|---|---|---|---|---|---|
| 9.8-10.4 | 20° C. | 12.5 g/L | 2.1 | 81.9% | 10.0% |

Example 9

Preparation of 1,16-Hexadecanedioic Acid Mono Benzyl Ester

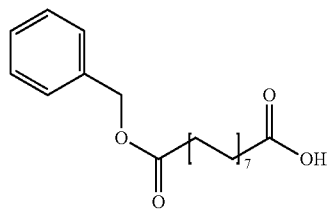

Hexadecanedioic acid (20.0 g, 69.8 mmol) and Dowex$^R$ were suspended in n-octane and heated to reflux. Benzyl formate (22.0 g, 162 mmol) was added. After 6 hours additional benzyl formate (22.0 g, 162 mmol) was added. The heating was continued for 50 hours. The reaction mixture was filtered at 80° C. The filtrate was cooled to 20° C., and the precipitate was collected by filtration. The crude product (20.2 g) was suspended in dichloromethane (220 ml) at 20° C. for 4 hours. The suspension was filtered, and the filtrate was evacuated to dryness at 20-30° C. The resulting solid (13.9 g) was recrystallised from 2-propanol (140 ml). The product was isolated by filtration, and dried to constant weight under reduced pressure at 30-40° C. Yield: 10.2 g (39%) of white material.

Example 10

Preparation of (S)-2-(15-benzyloxycarbonyl-pentadecanoylamino)pentanedioic acid 5-benzyl ester 1-(2,5-dioxo-pyrrolidin-1-yl) ester

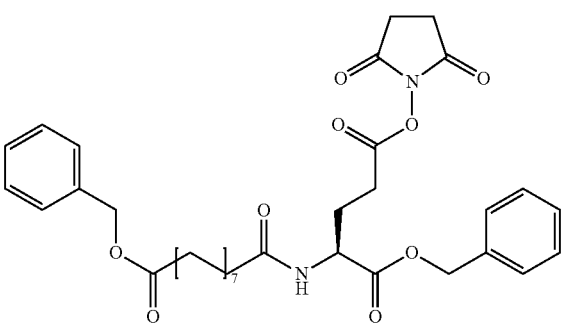

1,16-hexadecanedioic acid mono benzyl ester (20.0 g, 53.1 mmol) was dissolved in acetone at 35-40° C. N-Hydroxysuccinimide (6.42 g, 55.8 mmol) was added. To the resulting solution dicyclohexylcarbodiimide (DCC) (12.1 g, 58.4 mmol) was added. The reaction mixture was stirred for 3-4 hours at 35° C. To the resulting suspension triethylamine (7.40 ml, 53.1 mmol) and L-glutamic acid α-benzyl ester (12.6 g/53.1 mmol) were added. The reaction mixture was stirred for 8-16 hours at 35-40° C. The reaction mixture was cooled to 20-25° C. Methanesulfonic acid (3.45 ml, 53.1 mmol) and DCC (12.1 g, 53.1 mmol) were added. The reaction mixture was stirred for 8-16 hours at 20-25° C. The reaction mixture was filtered, and the filtrate evacuated to dryness. The residue was partitioned between water (100 ml) and toluene (200 ml). The toluene phase was dried by distilling off water. Silica gel (20 g) was added to the residue. The suspension was stirred for 30 minutes at 20-25° C., subsequently filtered. The volume of the filtrate was reduced to app. 100-120 ml by evaporation under reduced pressure. N-heptane (150 ml) was added over a period of 15-30 minutes. The resulting suspension was stirred for 2 hours. The product was isolated by filtration, and dried to constant weight under reduced pressure at 20-25° C. Yield 21 g (58%) of white material.

Example 11

Preparation of (22S)-22-carboxy-1-[(2,5-dioxo-1-pyrrolidinyl)oxy]-1,10,19,24-tetraoxo-3,6,12,15-tetraoxa-9,18,23-triazahendicontan-39-oic acid (Compound 2)

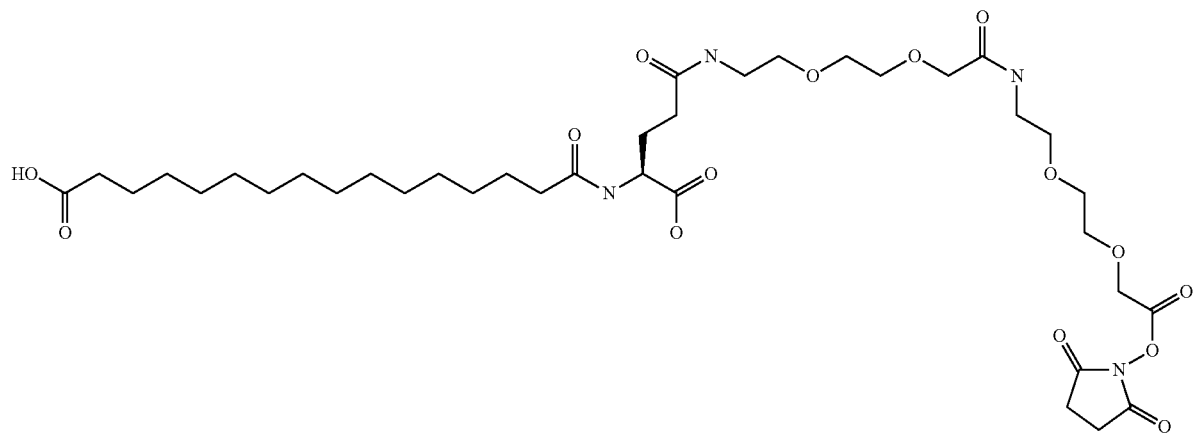

Compound 2

(S)-2-(15-benzyloxycarbonyl-pentadecanoylamino)-pentanedioic acid 5-benzyl ester 1-(2,5-dioxo-pyrrolidin-1-yl) ester (4 g, 5.77 mmol) and 17-Amino-10-oxo-3,6,12,15-tetraoxa-9-azaheptadecan-1-oic acid (1.8 g, 5.95 mmol) were suspended in NMP (20 ml) and the mixture was stirred for 16 hr. N-hydroxysuccinimide (0.94 g, 8.12 mmol) and N,N-dicyclohexylcarbodiimide (2.15, 10 mmol) were added, and the resulting solution was stirred for app. 16 hr. Water (150 ml) and ethylacetate (30 ml) were added and the organic phase collected, dried over MgSO$_4$ and evaporated in vacuo. The semisolid was redissolved in acetone, Pd/C (0.5 g) was added and the mixture was hydrogenated for 2 hr. The mixture was filtered and evaporated in vacuo. Yield 3.69 g (88%).

Example 12

Selective Acylation of [Aib$^8$, Arg$^{34}$]GLP-1(7-37) with compound 2

Acylation was performed as described in the general acylation method as described in Example 6.

The conditions used were:

| pH | Temp. | Conc. peptide | eq. acylating agent | Lys-26 acylated | Nα- and Lys-26 diacylated |
|---|---|---|---|---|---|
| 11.25 | 20° C. | 12.5 g/L | 1.93 | 92.8% | 1.3% |

Example 13

Solid Phase Synthesis of Acylating Agent Compounds 3-5

Compounds 3-5 were synthesised on a solid phase using the below mentioned steps:

Loading:

2-Chlorotrityl chloride resin was swelled in DCM in a solid phase peptide reactor equipped with a centred mechanically teflon-coated stirrer. A solution of Fmoc-8-amino-3,6-dioxanoic acid (1 eq.) and DIPEA (1.1 eq) in DCM was added and the resulting mixture was stirred 16 hr. at r.t. The resin was drained and unreacted sites on the resin were capped with a mixture of DCM:MeOH:DIPEA (80:15:5), and subsequently washed with DCM and NMP.

Elongation:

1) Deprotection Procedure:

Deprotection of Fmoc-group on the resin; the resin was treated with piperidine in NMP (20% solution) and washed with NMP.

2) Subsequent Coupling Procedure:

The amino acid or benzyl 18-({(1S)-1-[(benzyloxy)carbonyl]-4-[(2,5-dioxo-1-pyrrolidinyl)oxy]-4-oxobutyl}amino)-18-oxooctadecanoate (2 eq. compared to original resin loading) was dissolved in NMP. The amino acid was preactivated with N-hydroxybenzotriazole (HOBt) and N,N'-diisopropylcarbodiimide (DIPCDI) for 15-30 min or the succinimide ester of the amino acid or benzyl 18-({(1S)-1-[(benzyloxy)carbonyl]-4-[(2,5-dioxo-1-pyrrolidinyl)oxy]-4-oxobutyl}amino)-18-oxooctadecanoate was dissolved in NMP, and then added to the resin. Optionally, after 30 to 60 min DIPEA was added and the mixture was stirred from between 1 hr to 16 hr at r.t. If a test for free amine was negative (Kaiser test) the coupling cycle was finished, the resin was washed with NMP and ready to move on to the consecutive cycle step.

Cleavage Procedure:

The resin was washed with DCM:MeOH (1:1), DCM and treated with a mixture of DCM:TIPS:TFA (95.5:2.5:2) for 10 min, the cleaving mixture was drained into DIPEA to obtain a solution with pH>7. The cleavage treatment was repeated. The crude solution was washed with citric acid (aq. 10% 3×), Brine (1×), dried over MgSO$_4$ and evaporated in vacuo. The oily residue was co-evaporated twice with toluene.

Activation:

The resulting residue and N-hydroxysuccinimide (1.1 eq) was dissolved in EtOAc. N,N'-dicyclohexylcarbodiimide (1.3 eq) was added and the mixture was stirred for app. 16 hr. The mixture was filtered and evaporated in vacuo.

Deprotection: of Tert-Butyl Esters:

The semisolid was dissolved in TFA and DCM, stirred for 2 hr. and subsequently evaporated in vacuo and coevaporated twice with toluene, before recrystallisation from 2-propanol.

Deprotection of Benzyl Esters:

The semisolid was dissolved in 2-propanol, Pd/C was added and the resulting mixture was hydrogenated for 2 hr., heated to 45° C., filtered and cooled to 5° C. The resulting crystals were collected by filtration.

Example 14

Preparation of Compound 3: 19-((S)-1-Carboxy-3-{2-[2-({2-[2-(2,5-dioxo-pyrrolidin-1-yloxycarbonyl-methoxy)ethoxy]-ethylcarbamoyl}methoxy)ethoxy] ethylcarbamoyl}propylcarbamoyl)nonadecanoic acid The compound was prepared on solid phase according to the general procedure described in Example 13, using 1,20-eicosanedioic acid mono t-butyl ester, N-(9-fluorenylmethyloxycarbonyl)-L-glutamic-acid α-t-butyl ester and 8-(9-fluorenylmethyloxycarbonyl-amino)-3,6-dioxaoctanoic acid.

Example 15

Selective Acylation of [Aib$^8$, Arg$^{34}$]GLP-1(7-37) Peptide with Compound 3

Acylation was performed as described in the general acylation method as described in Example 6.

The conditions used were:

| pH | Temp. | Conc. peptide | eq. acylating agent | Lys-26 acylated | Nα- and Lys-26 diacylated |
|---|---|---|---|---|---|
| 11.25 | 20° C. | 12.5 g/L | 1.6 | 84.2% | 4.0% |

Compound 3

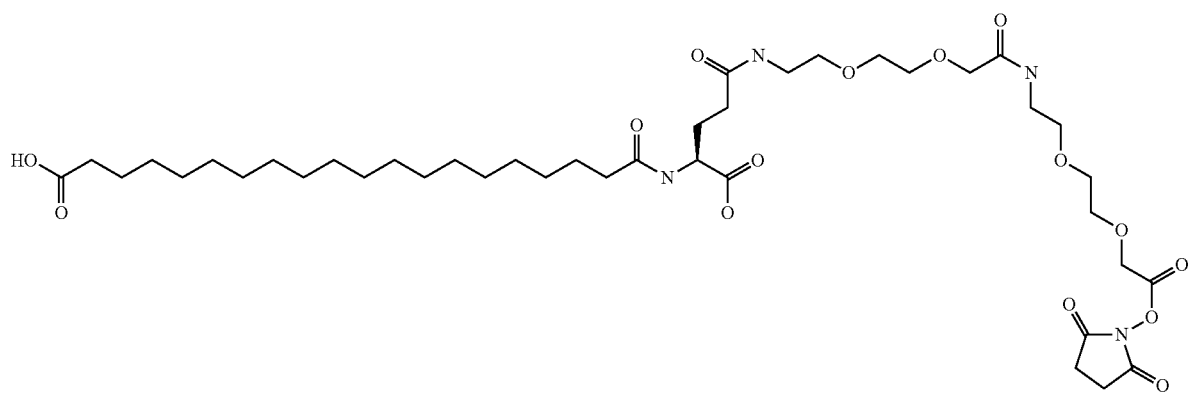

Example 16

Preparation of Compound 4 17-((S)-1-Carboxy-3-{2-[2-(2,5-dioxo-pyrrolidin-1-yloxycarbonyl-methoxy)-ethoxy]-ethylcarbamoyl}-propylcarbamoyl)heptadecanoic acid

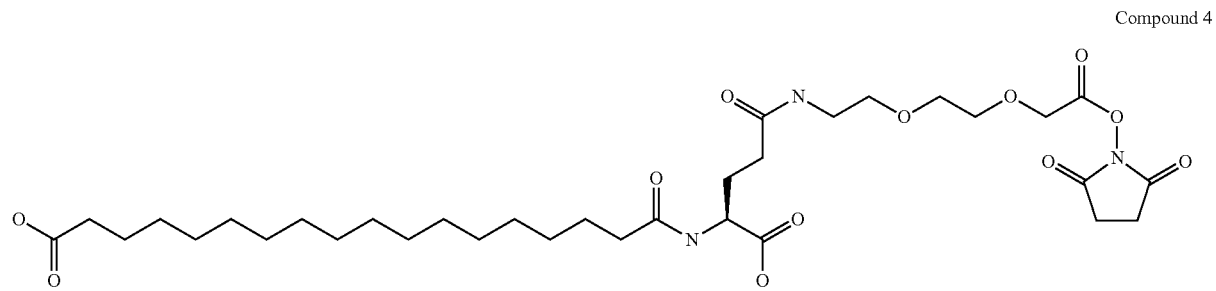 [SMILES: O=C(O)CCCCCCCCCCCCCCCCC(=O)N[C@@H](CCC(=O)NCCOCCOCC(=O)ON1C(=O)CCC1=O)C(=O)O]

Compound 4

The compound was prepared on solid support according to the general procedure described in Example 13, using benzyl 18-({(1S)-1-[(benzyloxy)carbonyl]-4-[(2,5-dioxo-1-pyrrolidinyl)oxy]-4-oxobutyl}amino)-18-oxooctadecanoate and 8-(9-fluorenylmethyloxycarbonyl-amino)-3,6-dioxaoctanoic acid.

Example 17

Selective Acylation of [Aib$^8$, Arg$^{34}$]GLP-1(7-37) Peptide with Compound 4

Acylation was performed as described in the general acylation method as described in Example 6.

The conditions used were:

| pH | Temp. | Conc. peptide | eq. acylating agent | Lys-26 acylated | Nα- and Lys-26 diacylated |
|---|---|---|---|---|---|
| 11.25 | 20° C. | 12.5 g/L | 2.0 eq | 96.9% | 1.72% |

Example 18

Preparation of Compound 5 17-((S)-1-Carboxy-3-{2-[2-({2-[2-({2-[2-(2,5-dioxo-pyrrolidin-1-yloxycarbonylmethoxy)-ethoxy]-ethylcarbamoyl}-methoxy)-ethoxy]-ethylcarbamoyl}-methoxy)-ethoxy]-ethylcarbamoyl}-propylcarbamoyl)-heptadecanoic acid

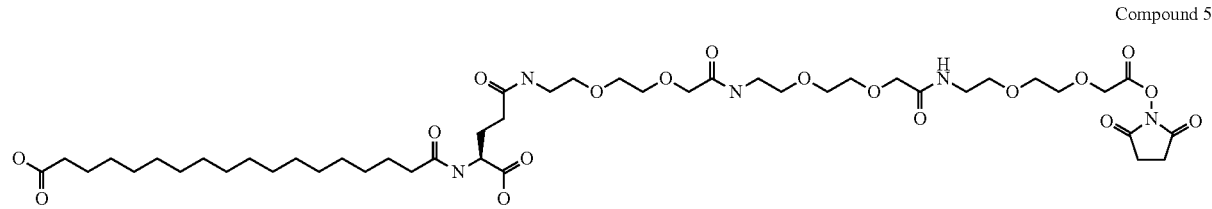 [SMILES: O=C(O)CCCCCCCCCCCCCCCCC(=O)N[C@@H](CCC(=O)NCCOCCOCC(=O)NCCOCCOCC(=O)NCCOCCOCC(=O)ON1C(=O)CCC1=O)C(=O)O]

Compound 5

The compound was prepared on solid support according to the general procedure described in Example 13, using benzyl 18-({(1S)-1-[(benzyloxy)carbonyl]-4-[(2,5-dioxo-1-pyrrolidinyl)oxy]-4-oxobutyl}amino)-18-oxooctadecanoate and 8-(9-fluorenylmethyloxycarbonyl-amino)-3,6-dioxaoctanoic acid.

Example 19

Selective Acylation of [Aib$^8$, Arg$^{34}$]GLP-1(7-37) Peptide with Compound 5

Acylation was performed as described in the general acylation method as described in Example 6.
The conditions used were:

| pH | Temp. | Conc. peptide | eq. acylating agent | Lys-26 acylated | Nα- and Lys-26 diacylated |
|---|---|---|---|---|---|
| 11.25 | 20° C. | 12.5 g/L | 4.0 eq | 66.7% | 2.83% |

Example 20

Preparation of Compound 6

The compound was prepared as described in Example 14).

Example 21

Selective Acylation of Aib$^8$, Arg$^{34}$]GLP-1(7-37) with Compound 6

Acylation was performed as described in the general acylation method as described in Example 6.
The conditions used were:

| pH | Temp. | Conc. peptide | eq. acylating agent | Lys-26 acylated | Nα- and Lys-26 diacylated |
|---|---|---|---|---|---|
| 11.25 | 20° C. | 12.5 g/L | 2.0 | 97.6% | 1.1% |

Example 22

Preparation of (S)-2-(15-carboxy-pentadecanoylamino)-pentanedioic acid 5-(2,5-dioxo-pyrrolidin-1-yl) ester (S)-2-(15-benzyloxycarbonyl-pentadecanoylamino)-pentanedioic acid 5-benzyl ester 1-(2,5-dioxo-pyrrolidin-1-yl) ester (5.0 g, 7.3 mmol) was dissolved in acetone (95 ml) containing trifluoroacetic acid (95 µl). Palladium on carbon, 10% (0.50 g) was added. Under stirring at 30-35° C. hydrogen was added. When the consumption of hydrogen stopped the reaction mixture was filtered. The filtrate was cooled to 20° C.

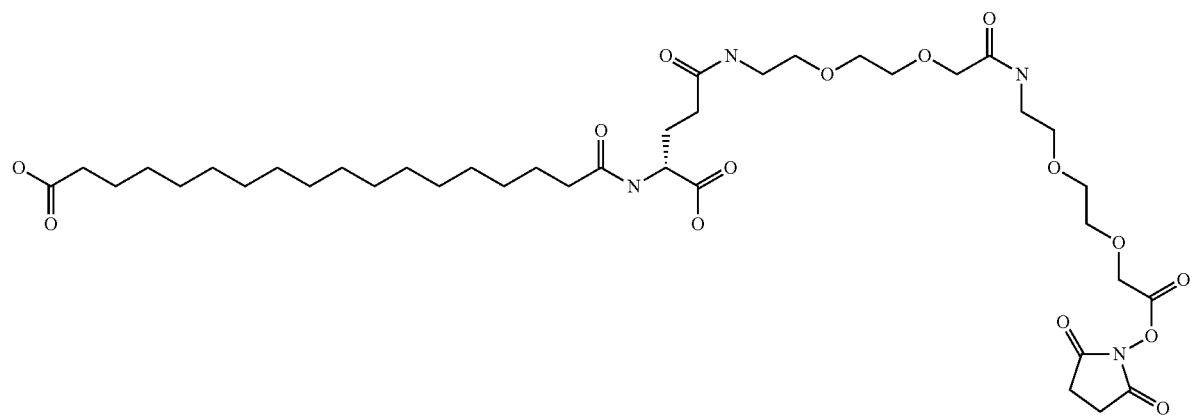

Compound 6 and n-heptane (140 ml) was added over a period of 15-30 minutes. The resulting suspension was cooled to 0-5° C. for 2-3 hours. The product was isolated by filtration, and dried to constant weight under reduced pressure at 20-25° C. Yield 3 g (84%) of white material.

The product was analysed by proton NMR (Bruker 600 MHz) using acetone-d6 as solvent.

Proton NMR assignments from the 1D spectrum (internal reference is TMS at δ 0.0 ppm):

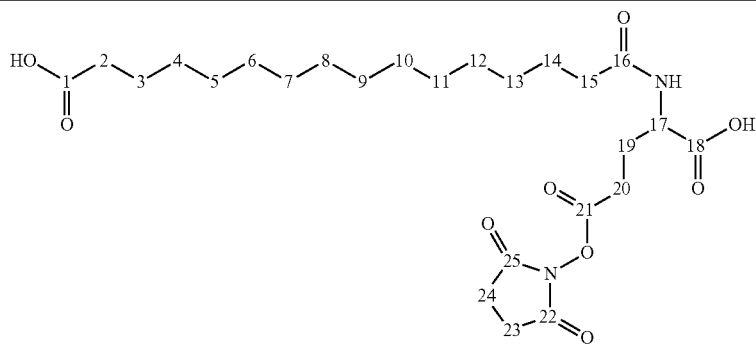

| $^1$H | Chemical Shift δ (ppm) | Integral | Coupling Pattern | Coupling Constants $^nJ_{HH}$ (Hz) |
|---|---|---|---|---|
| H2 | 2.28 | 2H | t | $^3J_{HH} = 7.5$ |
| H3/H14 | 1.60 | 4H | m | ND |
| H4-H13 | 1.29 | 20H | m | ND |
| H15 | 2.26 | 2H | dt | $^2J_{HH} = 2.5, ^3J_{HH} = 7.5$ |
| H17 | 4.59 | 1H | ddd | $^3J_{HH} = 8.0/7.5/5.2$ |
| H19 | 2.31/2.10 | 2H | m | ND |
| H20 | 2.82/2.75 | 2H | ddd | $^2J_{HH} = 16.5, ^3J_{HH} = 10.0/6.0$ |
| H23/H24 | 2.88 | 4H | s | — |
| NH | 7.37 | 1H | d | $^3J_{HH} = 7.5$ |

Example 23

Acylation of the Human Insulin desB30 ε-amino-group in lysine in position B29 with (S)-2-(15-carboxypentadecanoylamino)pentanedioic acid 5-(2,5-dioxopyrrolidin-1-yl)ester 4 g of desB30 human insulin was suspended in 64 g of purified water. 1.85 ml of triethyl amine (TEA) was added to dissolve desB30 human insulin and to raise the pH to 11.4-12.0. The solution was cooled to 2-5° C.

448 mg of L-2-(15-carboxy-pentadecanoylamino)-pentanedioic acid 5-(2,5-dioxo-pyrrolidin-1-yl) ester was dissolved in 3.5 g NMP (N-methyl-2-pyrrolidon) stabilised with 10 μl 5% sulphuric acid.

The desB30 human insulin solution was stirred, and the solution of (S)-2-(15-carboxypentadecanoylamino)pentanedioic acid 5-(2,5-dioxopyrrolidin-1-yl) ester was added over a 20 min period, while keeping the temperature low.

After the addition of (S)-2-(15-carboxy-pentadecanoylamino)pentanedioic acid 5-(2,5-dioxo-pyrrolidin-1-yl) ester the reaction mixture was diluted with 2.5 weight of a solution consisting of: Tris-hydroxymethylaminomethan (20 mmol/kg), ammonium acetate (30 mmol/kg), ethanol 42.5% w/w, the rest purified water, pH 7.5

After dilution the pH was adjusted to 7.5 by slowly adding 1 M acetic acid, while stirring. Analysis by HPLC demonstrates the formation of 72.11% Lys$^{B29}$(Nε-hexadecandioyl-γ-glutamyl) des(B30) human insulin with 14.22% residual desB30 human insulin.

Example 24

Acylation of the Human Insulin desB30 ε-Amino-group in Lysine in Position B29 with 15-[3-(2,5-Dioxopyrrolidin-1-yloxycarbonyl)-propylcarbamoyl] pentadecanoic acid 35 g of desB30 human insulin was suspended in 539 g of cold 14 mM EDTA. The solution was cooled to 2-5° C. 15.6 g 4 M NaOH and 21.9 g of triethyl amine (TEA) was added to dissolve desB30 human insulin and to raise the pH to 12.7.

4.1 g of 15-[3-(2,5-Dioxopyrrolidin-1-yloxycarbonyl)-propylcarbamoyl]pentadecanoic acid was dissolved in 82.1 g NMP (N-methyl-2-pyrrolidon) stabilised with 10 μl 5% sulphuric acid. The desB30 human insulin solution was stirred, and the solution of 15-[3-(2,5-Dioxopyrrolidin-1-yloxycarbonyl)-propylcarbamoyl]pentadecanoic acid was added over a 20 min period, while keeping the temperature low.

After the addition of 15-(3-Carboxypropylcarbamoyl)pentadecanoic acid benzyl ester the reaction mixture was diluted with 2.5 weight of a solution consisting of: Tris-hydroxymethylaminomethan (20 mmol/kg), ammonium acetate (30 mmol/kg), ethanol 42.5% w/w, the rest purified water, pH 7.0

After dilution the pH was adjusted to 7.6 by slowly adding 1 M acetic acid, while stirring and allowing temperature to rise to room temperature.

Analysis by HPLC demonstrates the formation of 68.1% Lys$^{B29}$(Nε-hexadecandioyl-γ-glutamyl) des(B30) human insulin.

Example 25

Analytical HPLC

A 150×4.6 mm I.D. column was packed with a octyldimethylsilyl substituted silica having pore size of about 100 Å and particle diameter of about 3.5 μm and was equilibrated at 40° C. at a flow rate of 1 ml/min with a mixture consisting of 1) a buffer of 20 mM NaH$_2$PO$_4$.H$_2$O and 100 mmol Na$_2$SO$_4$ adjusted to pH 5.9 with NaOH in the aqueous buffer and 2) acetonitrile solvent containing 42.8% w/w acetonitrile, to make 25% (w/w) acetonitrile.

When analysed, Lys$^{B29}$(Nε-hexadecandioyl-γ-glutamyl)des(B30) human insulin emerged from the column after about 20 min. When analysed, desB30 human insulin emerged from the column after about 6 min.

Example 26

Preparation of 19-((S)-1-Carboxy-3-{2-[2-({2-[2-(2, 5-dioxo-pyrrolidin-1-yloxycarbonylmethoxy)ethoxy]ethylcarbamoyl}methoxy)ethoxy]ethylcarbamoyl}-propylcarbamoyl)nonadecanoic acid (Alternative Name: Eicosanedioyl-gGlu-OEGOEG-OSu) Solution Phase Method LCMS Method (LCMS):

A Waters Micromass ZQ mass spectrometer was used to identify the mass of the sample after elution from a Waters Alliance HT HPLC system.

Eluents:
A: 0.1% Trifluoroacetic acid in water
B: 0.1% Trifluoroacetic acid in acetonitrile
Column: Phenomenex, Jupiter C4 50×4.60 mm, id: 5 μm
Gradient: 10%-90% B over 7.5 min at 1.0 ml/min
Column: Phenomenex, Jupiter 5μ C4 300 Å 50×4.60 mm
LC method: 10-90% B 10 min: A: 0.1% CH$_3$CN B: CH$_3$CN:
0-7.5 min: 10-90% B
7.5-8.5 min: 90-10% B
8.5-9.5 min 10% B
flow: 1 ml/min
9.5-10.00 min 10% B
flow: 0.1 ml/min Eicosanedioic acid tert-butyl ester N-hydroxysuccinimide ester

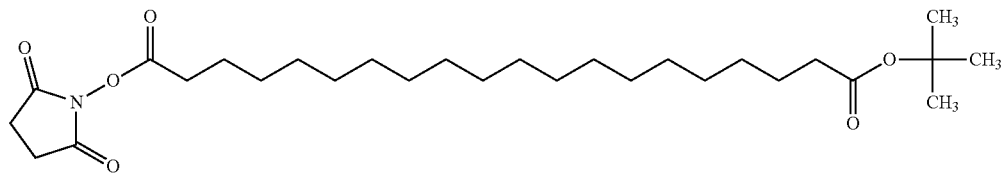 [SMILES: CC(C)(C)OC(=O)CCCCCCCCCCCCCCCCCCC(=O)ON1C(=O)CCC1=O]

Eicosanedioic acid mono-tert-butyl ester (5 g, 12.54 mmol) and TSTU (4.53 g, 15.05 mmol) were mixed in THF (50 mL), DIPEA (2.62 mL) was added and the resulting cloudy mixture was stirred at RT for 2 h, then DMF (30 mL) was added resulting in a clear solution which was further stirred overnight. The resulting mixture was evaporated to almost dryness and the residue was mixed with cold acetonitrile resulting in the precipitation of a precipitate. This was filtered off and dried in vacuo overnight, affording 6.01 g (97%) of icosanedioic acid tert-butyl ester N-hydroxysuccinimide ester.

MS (electrospray): m/z: 440 (M-56 (tBu)).

(S)-2-(19-tert-Butoxycarbonylnonadecanoylamino)pentanedioic acid 1-tert-butyl ester

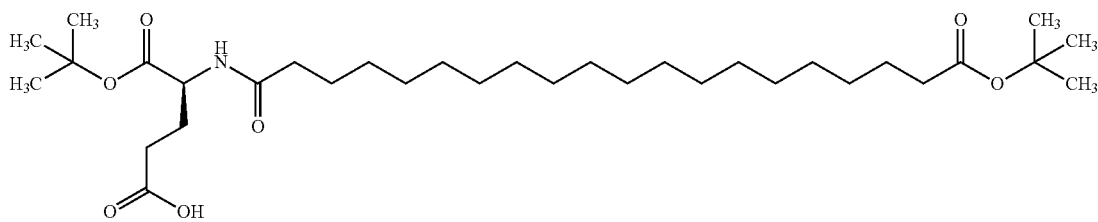 [SMILES: CC(C)(C)OC(=O)CCCCCCCCCCCCCCCCCCC(=O)N[C@@H](CCC(=O)O)C(=O)OC(C)(C)C]

Eicosanedioic acid tert-butyl ester 2,5-dioxo-pyrrolidin-1-yl ester (6.01 g, 12.124 mmol) was dissolved in THF (150 mL) and mixed with a slurry of H-Glu-OtBu (2.71 g, 13.33 mmol) in DMF/water (1/1, 40 mL). This resulted in a gel-like solution which was heated to give a clear solution that was stirred at RT for 3 h. Then the solution was evaporated, 100 mL of water was added and the mixture was heated to 60° C. which resulted in a solution which crystallised on cooling. The precipitate was recrystallised from acetonitrile and the crystals were dried in vacuum. Yield 6.82 g (96%).

MS (electrospray): m/z 584 (M+1).

(S)-2-(19-tert-Butoxycarbonylnonadecanoylamino) pentanedioic acid 1-tert-butyl ester 542,5-dioxopyrrolidin-1-yl) ester

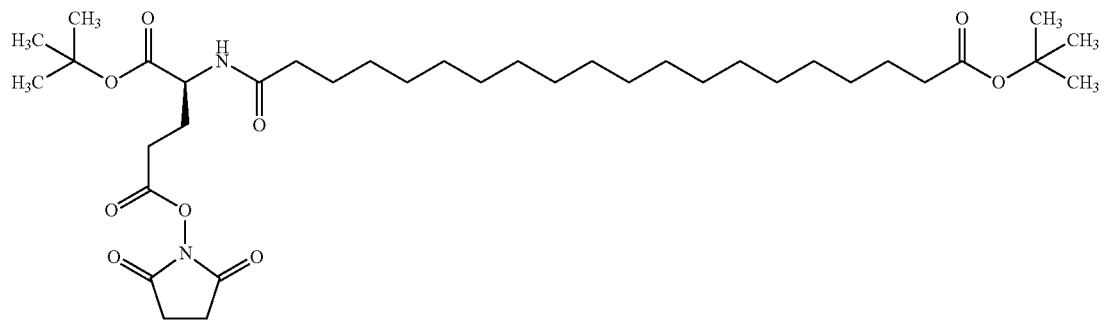 [SMILES: CC(C)(C)OC(=O)CCCCCCCCCCCCCCCCCCC(=O)N[C@@H](CCC(=O)ON1C(=O)CCC1=O)C(=O)OC(C)(C)C]

(S)-2-(19-tert-Butoxycarbonylnonadecanoylamino)pentanedioic acid 1-tert-butyl ester (6.52 g, 11.17 mmol) was dissolved in THF (100 mL), DIPEA (2.14 mL) was added followed by a solution of TSTU (3.70 g, 12.29 mmol) in acetonitrile (25 mL). The mixture was stirred overnight at RT, then it was evaporated, resulting in a brownish residue which was recrystallised from acetonitrile. After cooling overnight at 5° C. a powder was formed. This was dissolved in THF and dried with MgSO$_4$, filtered and evaporated to dryness to afford 6.17 g (81%) of the title compound.

MS (electrospray): m/z: 681 (M+1).

19-{(S)-1-tert-Butoxycarbonyl-3-[2-(2-{[2-(2-carboxymethoxyethoxy)ethylcarbamoyl]-methoxy}ethoxy)ethylcarbamoyl] propylcarbamoyl}nonadecanoic acid tert-butyl ester (Alternative Name: $^t$Bu-Eicosanedioyl-qGlu(O$^t$Bu)-OEG-OEG-OH)

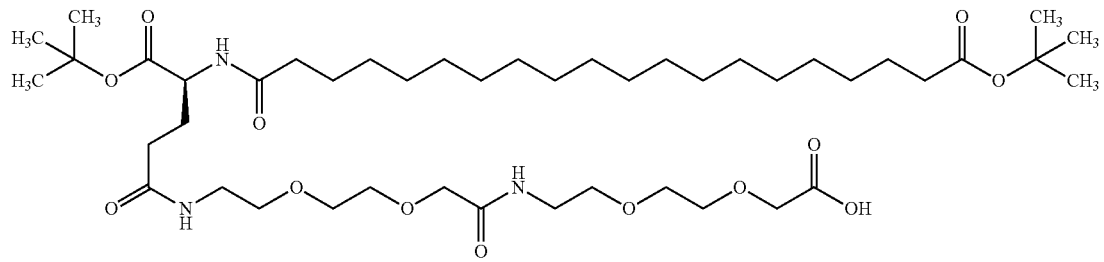 [SMILES: CC(C)(C)OC(=O)CCCCCCCCCCCCCCCCCCC(=O)N[C@@H](CCC(=O)NCCOCCOCC(=O)NCCOCCOCC(=O)O)C(=O)OC(C)(C)C]

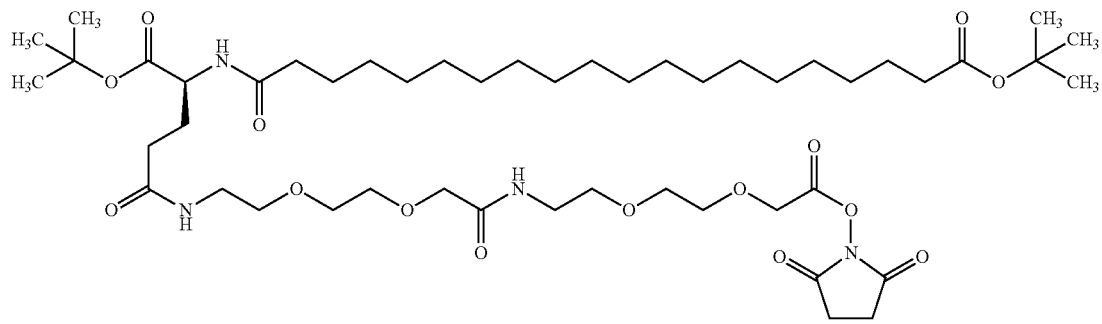 [SMILES: CC(C)(C)OC(=O)CCCCCCCCCCCCCCCCCCC(=O)N[C@@H](CCC(=O)NCCOCCOCC(=O)NCCOCCOCC(=O)ON1C(=O)CCC1=O)C(=O)OC(C)(C)C]

To a solution of 19-{(S)-1-tert-Butoxycarbonyl-3-[2-(2-{[2-(2-carboxymethoxyethoxy)ethylcarbamoyl]methoxy}ethoxy)ethylcarbamoyl]propylcarbamoyl}nonadecanoic acid tert-butyl ester (3.1 g) in acetonitrile (50 ml) was added TSTU (1.39 g) and DIPEA (0.91 ml). The mixture was stirred at room temperature over night and then concentrated in vacuo. To the residue was added aqueous 0.1 N HCl (100 ml) and ethyl acetate (200 ml). The layers were separated and the aqueous layer was extracted with ethyl acetate (50 ml). The combined organic layers were washed with water and brine, dried (magnesium sulphate) and concentrated in vacuo to give an oil. Yield 99% (3.4 g).

LCMS: Theoretical mass: 971.2 Found: 971.8.

19-((S)-1-Carboxy-3-{2-[2-({2-[2-(2,5-dioxo-pyrrolidin-1-yloxycarbonylmethoxy)ethoxy]ethylcarbamoyl}methoxy)ethoxy]ethylcarbamoyl}propylcarbamoyl)nonadecanoic acid (Alternative Name: Eicosanedioyl-gGlu-OEG-OEG-OSu)

19-((S)-1-tert-Butoxycarbonyl-3-{2-[2-({2-[2-(2,5-dioxo-pyrrolidin-1-yloxycarbonylmethoxy)ethoxy]ethylcarbamoyl}methoxy)ethoxy]ethylcarbamoyl}propylcarbamoyl)nonadecanoic acid tert-butyl ester (3.4 g) was stirred in TFA (75 ml) for 45 min and then concentrated in vacuo. The residue was co-concentrated with toluene 3 times to give a solid. The residue was crystallised in 2-propanol and filtered to give a white crystalline compound. Yield 80% (2.4 g). LCMS: Theoretical mass: 859.03 Found: 859.44.

Alternatively, the acylation reagent can be prepared employing a solid phase method to prepare the intermediate 19-((S)-1-tert-butoxycarbonyl-3-{2-[2-({2-[2-(2,5-dioxo-pyrrolidin-1-yloxycarbonylmethoxy)ethoxy]ethylcarbamoyl}methoxy)ethoxy]ethylcarbamoyl}propylcarbamoyl)nonadecanoic acid tert-butyl ester (alternative name: ᵗBu-EicosanedioylgGlu(OᵗBu)-OEG-OEG-OH) as described in WO 2009/022005 followed by activation as Nhydroxysuccinimide ester and TFA cleavage (last two steps above).

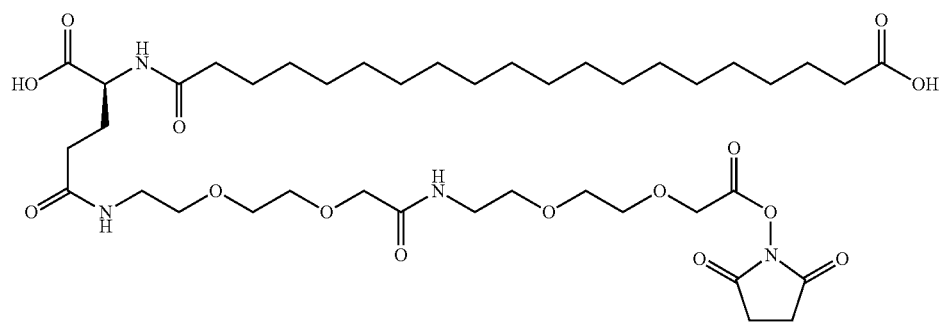 [SMILES: O=C(O)CCCCCCCCCCCCCCCCCCC(=O)N[C@@H](CCC(=O)NCCOCCOCC(=O)NCCOCCOCC(=O)ON1C(=O)CCC1=O)C(=O)O]

Example 27

Acylation of A14E, B25H, desB27, desB30 Human Insulin Using the Reagent 19-((S)-1-Carboxy-3-{2-[2-({2-[2-(2,5-dioxo-pyrrolidin-1-yloxycarbonyl-methoxy)ethoxy]ethylcarbamoyl}methoxy)ethoxy]ethylcarbamoyl}propylcarbamoyl)nonadecanoic acid (Alternative Name: Eicosanedioyl-gGlu-OEG-OEG-OSu)

Preparation of A14E, B25H, B29K((N(eps) Eicosanedioyl-gGlu-[2-(2-{2-[2-(2-aminoethoxy)ethoxy]acetylamino}ethoxy)ethoxy]acetyl)), desB27, desB30 human insulin (Alternative Name: A14E, B25H, B29K(N$^\epsilon$Eicosanedioyl-gGlu-OEG-OEG), desB27, desB30 human insulin)

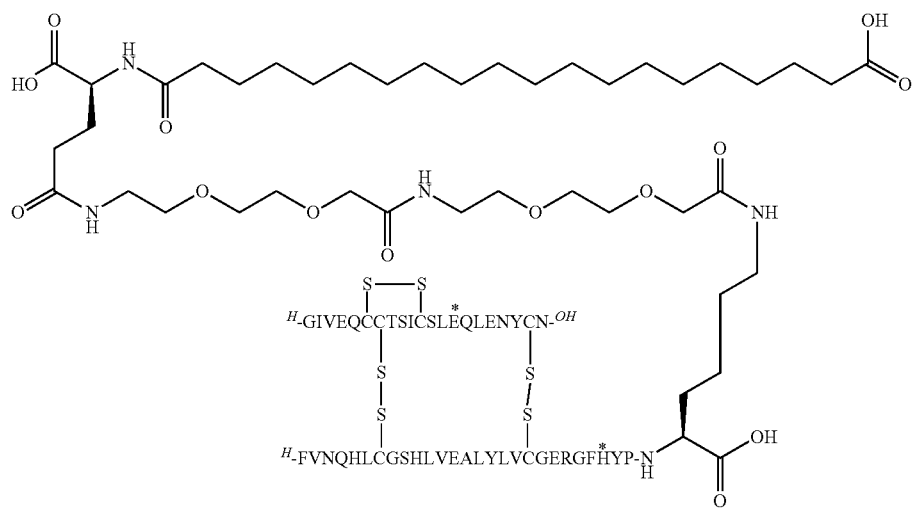

1 g (0.18 mmol) A14E, B25H, desB27, desB30 human insulin was dissolved in aqueous sodium carbonate (100 mM, 35 mL). pH was adjusted from 10.29 to 10.45 with 1 N NaOH. 19-((S)-1-Carboxy-3-{2-[2-({2-[2-(2,5-dioxo-pyrrolidin-1-yloxycarbonylmethoxy)ethoxy]ethylcarbamoyl}methoxy)ethoxy]ethylcarbamoyl}propylcarbamoyl)nonadecanoic acid (alternative name: Eicosanedioyl-gGlu-OEG-OEG-OSu) (190 mg, 0.22 mmol) dissolved in NMP (3.3 mL) was added. The mixture was stirred for 50 minutes at room temperature. Water (50 mL) was added and pH was adjusted to 4.4 with 1N hydrochloric acid. The precipitate was isolated by centrifugation, and the supernatant was decanted.

HPLC-MS of the precipitated product showed 26.9% unchanged insulin, 61.7% mono-acylated desired product (B29-acylated) and 11% diacylated product. There was no trace of the A1-mono-acylated product (eluting prior to the B29 acylated product) using this HPLC-MS method:

The precipitate was subsequently dissolved in water, containing 1% TFA, and acetonitrile and purified by RP HPLC (column: Phenomenex, Gemini, 5μ, C18, 110 A, 250×30 mm). Pure fractions were pooled and lyophilised. The lyophilised powder was dissolved in water and pH was adjusted to 8.0 using 0.1 N NaOH. Lyophilisation afforded the title insulin. HPLC-MS of the product showed only the mono-acylated desired product (B29-acylated) in 100% purity.

Example 28

Acylation of A14E, B25H, desB30 Human Insulin Using the Reagent 17-((S)-1-Carboxy-3-{2-[2-({2-[2-(2,5-dioxo-pyrrolidin-1-yloxycarbonylmethoxy)ethoxy]ethylcarbamoyl}methoxy)ethoxy]ethylcarbamoyl}propylcarbamoyl)heptadecanoic acid (Alternative Name: Octadecanedioyl-gGlu-OEG-OEG-OSu) at pH 11.5 and Room Temperature Preparation of A14E, B25H, B29K((N$^\epsilon$Octadecanedioyl-gGlu-[2-(2-{2-[2-(2-aminoethoxy)ethoxy]acetylamino}ethoxy)ethoxy]acetyl)), desB30 Human Insulin (Alternative Name: A14E, B25H, B29K (N$^\epsilon$Octadecanedioyl-gGlu-OEG-OEG), desB30 Human Insulin)

A14E, B25H, desB30 human insulin was dissolved in water to a conc. of 20 g/l at room temperature. Solid sodium phosphate was added to a conc. of 15 mM and pH was adjusted to 11.5 with NaOH. Acylation reagent (octadecanedioyl-gGlu-OEG-OEG-OSu) was dissolved in NMP to a conc. of 0.2 g/ml and added stepwise to the insulin solution under agitation. pH was kept constant at 11.5 by continuously addition of NaOH during the reaction. Samples were withdrawn and analyzed by RP-HPLC during the reaction. Results are shown below in table 28.1.

TABLE 28.1

B29 MA and A1 MA and is short hand notations of monoacylated in position B29K and the N-terminal amino group of A1, respectively. Likewise, sum of diacylated is written as DA.

| Mole equivalents acylation reagent relative to insulin | % unchanged | % B29 MA | % A1 MA | % sum DA | % B29 MA of sum (MA + DA) |
|---|---|---|---|---|---|
| 0.00 | 94.8 | | | | |
| 0.59 | 61.7 | 29.8 | 1.4 | 2.2 | 89 |
| 1.18 | 33.1 | 52.4 | 1.9 | 6.7 | 86 |
| 1.76 | 14.8 | 64.4 | 1.6 | 12.4 | 82 |
| 2.35 | 5.8 | 66.4 | 1.1 | 18.9 | 77 |
| 2.94 | 1.8 | 62.4 | 0.6 | 25.7 | 70 |

Example 29

Acylation of A14E, B25H, desB30 Human Insulin Using the Reagent 17-((S)-1-Carboxy-3-{2-[2-({2-[2-(2,5-dioxo-pyrrolidin-1-yloxycarbonylmethoxy)ethoxy]ethylcarbamoyl}methoxy)ethoxy]ethylcarbamoyl}propylcarbamoyl)heptadecanoic acid (Alternative Name: Octadecanedioyl-gGlu-OEG-OEG-OSu) at 2° C. at pH 11.25; 11.50 and 11.75

Preparation of A14E, B25H, B29K((N$^\epsilon$Octadecanedioyl-gGlu-[2-(2-{2-[2-(2-aminoethoxy)ethoxy]acetylamino}ethoxy)ethoxy]acetyl)), desB30 Human Insulin (Alternative Name: A14E, B25H, B29K(N$^\epsilon$Octadecanedioyl-gGlu-OEG-OEG), desB30 Human Insulin)

A14E, B25H, desB30 human insulin was dissolved in water to a conc. of 20 g/l at 2° C. in 3 different experiments and pH adjusted to 11.25, 11.50 and 11.75, respectively, with NaOH. Acylation reagent (octadecanedioyl-gGlu-OEG-OEG-OSu) was dissolved in NMP to a conc. of 0.2 g/ml and added stepwise to the insulin solution under agitation. pH was kept constant at the respective pH values by continuously addition of NaOH during the reaction. Samples were withdrawn and analyzed by RP-HPLC during the reaction. Results are shown below in table 29.1, 29.2, and 29.3, respectively.

TABLE 29.1 pH 11.25 acylation

| Mole equivalents acylation reagent relative to insulin | % unchanged | % B29 MA | % A1 MA | % sum DA | % B29 MA of sum (MA + DA) |
|---|---|---|---|---|---|
| 0.00 | 95.8 | | | | |
| 0.37 | 67.8 | 19.5 | 4.1 | 2.3 | 75 |
| 0.74 | 45.1 | 32.9 | 6.0 | 8.3 | 70 |
| 1.11 | 27.8 | 41.2 | 6.3 | 16.7 | 64 |
| 1.48 | 15.4 | 44.6 | 5.3 | 26.1 | 59 |
| 1.85 | 7.1 | 42.9 | 3.7 | 36.5 | 52 |
| 2.22 | 2.6 | 38.0 | 2.0 | 45.3 | 45 |
| 2.59 | 0.8 | 30.9 | 0.9 | 52.5 | 37 |

TABLE 29.2 pH 11.50 acylation

| Mole equivalents acylation reagent relative to insulin | % unchanged | % B29 MA | % A1 MA | % sum DA | % B29 MA of sum (MA + DA) |
|---|---|---|---|---|---|
| 0.00 | 95.8 | | | | |
| 0.38 | 68.0 | 21.7 | 3.0 | 1.7 | 82 |
| 0.77 | 44.6 | 38.1 | 4.5 | 6.2 | 78 |
| 1.15 | 26.3 | 48.9 | 4.7 | 13.0 | 73 |
| 1.54 | 13.2 | 54.6 | 3.7 | 21.1 | 69 |
| 1.92 | 5.7 | 54.1 | 2.4 | 30.0 | 63 |
| 2.31 | 2.1 | 49.0 | 1.3 | 38.6 | 55 |
| 2.69 | 0.8 | 41.0 | 0.7 | 46.0 | 47 |

TABLE 29.3 pH 11.75 acylation

| Mole equivalents acylation reagent relative to insulin | % unchanged | % B29 MA | % A1 MA | % sum DA | % B29 MA of sum (MA + DA) |
|---|---|---|---|---|---|
| 0.00 | 95.9 | | | | |
| 0.38 | 67.9 | 22.7 | 2.5 | 1.6 | 85 |
| 0.76 | 44.0 | 40.6 | 3.9 | 5.4 | 81 |
| 1.14 | 25.4 | 52.6 | 4.1 | 11.4 | 77 |
| 1.52 | 12.5 | 58.3 | 3.2 | 19.2 | 72 |
| 1.90 | 4.9 | 57.7 | 2.0 | 27.9 | 66 |
| 2.28 | 1.8 | 52.5 | 1.1 | 36.1 | 59 |
| 2.66 | 0.7 | 45.5 | 0.6 | 42.9 | 51 |

Example 30

Acylation of A14E, B16H, B25H, desB30 Human Insulin Using the Reagent 17-((S)-1-Carboxy-3-{2-[2-({2-[2-(2,5-dioxo-pyrrolidin-1-yloxycarbonylmethoxy)ethoxy]-ethylcarbamoyl}methoxy)ethoxy]ethylcarbamoyl}propylcarbamoyl)heptadecanoic acid (Alternative Name: Octadecanedioyl-gGlu-OEG-OEG-OSu) at pH 11.5 and Room Temperature Preparation of A14E, B16H, B25H, B29K((N$^\epsilon$Octadecanedioyl-gGlu-[2-(2-{2-[2-(2-aminoethoxy)ethoxy]acetylamino}ethoxy)ethoxy]acetyl)), desB30 Human Insulin (Alternative Name: A14E, B16H, B25H, B29K(N$^\epsilon$Octadecanedioyl-gGlu-OEG-OEG), desB30 Human Insulin)

A14E, B16H, B25H, desB30 human insulin was dissolved in water to a conc. of 20 g/l at room temperature. Solid sodium phosphate and EDTA was added to a conc. of 15 mM and 4 mM respectively. pH was adjusted to 11.5 with NaOH. Acylation reagent (octadecanedioylgGlu-OEG-OEG-OSu) was dissolved in NMP to a conc. of 0.2 g/ml and added stepwise to the insulin solution under agitation. pH was kept constant at 11.5 by continuously addition of NaOH during the reaction. Samples were withdrawn and analyzed by RP-HPLC during the reaction. Results are shown below in table 30.1.

TABLE 30.1

| Mole equivalents acylation reagent relative to insulin | % unchanged | % B29 MA | % A1 MA | % sum DA | % B29 MA of sum (MA + DA) |
|---|---|---|---|---|---|
| 0.00 | 92.9 | | | | |
| 0.56 | 56.6 | 31.3 | 2.0 | 2.1 | 88 |

TABLE 30.1-continued

| Mole equivalents acylation reagent relative to insulin | % unchanged | % B29 MA | % A1 MA | % sum DA | % B29 MA of sum (MA + DA) |
|---|---|---|---|---|---|
| 1.13 | 30.0 | 51.9 | 2.5 | 6.0 | 86 |
| 1.69 | 13.1 | 61.8 | 2.1 | 11.1 | 82 |
| 2.26 | 4.8 | 63.3 | 1.5 | 16.5 | 78 |
| 2.82 | 1.7 | 60.2 | 0.8 | 21.4 | 73 |

Example 31

Acylation of A14E, B25H, desB30 human insulin using the reagent 19-((S)-1-Carboxy-3-{2-[2-({2-[2-(2,5-dioxo-pyrrolidin-1-yloxycarbonylmethoxy)ethoxy]ethylcarbamoyl}methoxy)ethoxy]ethylcarbamoyl}propylcarbamoyl)nonadecanoic acid (Alternative Name: Eicosanedioyl-gGlu-OEG-OEG-OSu) at pH 11.5 and Room Temperature Preparation of A14E, B25H, B29K((N$^\epsilon$E-icosanedioyl-gGlu-[2-(2-{2-[2-(2-aminoethoxy)ethoxy]acetylamino}ethoxy)ethoxy]acetyl)), desB30 Human Insulin (Alternative Name: A14E, B25H, B29K(N$^\epsilon$Eicosanedioyl-gGlu-OEG-OEG), desB30 Human Insulin)

A14E, B25H, desB30 human insulin was dissolved in water to a conc. of 20 g/l at room temperature. Solid sodium phosphate and EDTA was added to a conc. of 15 mM and 4 mM respectively. pH was adjusted to 11.5 with NaOH. Acylation reagent (Eicosanedioyl-γGLUOEG-OEG) was dissolved in NMP to a conc. of 0.2 g/ml and added stepwise to the insulin solution under agitation. pH was kept constant at 11.5 by continuously addition of NaOH during the reaction. Samples were withdrawn and analyzed by RP-HPLC during the reaction. Results are shown below in table 31.1

TABLE 31.1

| Mole equivalents acylation reagent relative to insulin | % unchanged | % B29 MA | % A1 MA | % sum DA | % B29 MA of sum (MA + DA) |
|---|---|---|---|---|---|
| 0.00 | 95.1 | | | | |
| 0.54 | 67.8 | 22.4 | 1.3 | 1.9 | 88 |
| 1.09 | 46.4 | 38.4 | 1.8 | 5.2 | 85 |
| 1.63 | 30.0 | 48.9 | 1.9 | 9.3 | 81 |
| 2.18 | 18.2 | 54.5 | 1.7 | 14.0 | 78 |
| 2.72 | 10.7 | 56.1 | 1.4 | 19.2 | 73 |

The invention claimed is:

1. A method for selectively acylating one amino group in a peptide or protein which has two or more reactive nucleophilic functional groups, the method comprising:
   a) reacting in an aqueous media a peptide or protein having at least two reactive nucleophilic functional groups with an acylating agent of the general formula I

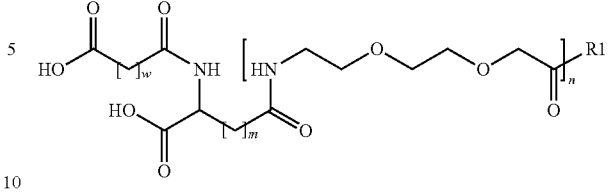

Formula I wherein
   n is 0-4
   m is 1-2
   w is 4-20
   R1 is a leaving group which when reacting said acylating agent with a free amine forms an amide bond between the carbonyl group attached to R1 and said amine,
   wherein pH in the aqueous media is between from greater than pH 8.0 to pH 14; and
   b) isolating the N-acylated peptide or protein,
wherein an N-acylated peptide or protein is obtained comprising at least one reactive nucleophilic functional group which is not acylated or only partially acylated.

2. The method according to claim 1, wherein said two or more reactive nucleophilic functional groups are amino-groups.

3. The method according to claim 1, wherein the pH of the aqueous reaction mixture is between pH 10 and pH 12.

4. The method according to claim 1, wherein the temperature of the reaction mixture during the acylation procedure is between −5° C. and 50° C.

5. The method according to claim 1, wherein the reagent is added over a period of between 30 and 60 minutes.

6. The method according to claim 1, wherein the acylation mixture is left for reaction for between 0 and 24 hours after addition of the acylation reagent.

7. The method according to claim 1, wherein the reaction is stopped by adjusting the pH to pH 6.5-8.0 after addition of the acylation reagent.

8. The method according to claim 1, wherein the peptide or protein is present in the reaction mixture in a concentration of at least 5.0 mg/ml.

9. The method according to claim 1, wherein the reaction mixture comprises a buffer.

10. The method according to claim 1, wherein the acylation reagent is added in a solution comprising the acylation agent dissolved in an inert solvent.

11. The method according to claim 1, wherein the reaction in step (a) is performed using the protein and the acylating agent of the formula I in a 1:1 to 1:5 molar ratio.

12. The method according to claim 1, wherein the peptide or protein to be acylated is a peptide or protein which is suitable for treating diabetes.

13. The method according to claim 1, wherein the peptide or protein to be acylated is a peptide or protein which is suitable for treating obesity.

14. The method according to claim 1, wherein the peptide or protein to be acylated is a glucagon-like peptide or an insulin.

15. The method according to claim 1, wherein an N-acylated peptide or protein is obtained comprising at least one free amino group which is not acylated.

16. The method according to claim 4, wherein the temperature of the reaction mixture during the acylation procedure is between 0° C. and 50° C.

17. The method according to claim 7, wherein the reaction is stopped by adjusting the pH to pH 7.5-8.0.

* * * * *